US007842515B2

(12) United States Patent
Zou et al.

(10) Patent No.: US 7,842,515 B2

(45) Date of Patent: Nov. 30, 2010

(54) NANO-STRUCTURED DEVICE FOR ANALYSIS OR SEPARATION, AND ITS PREPARATION AND APPLICATION

(75) Inventors: Fanglin Zou, Chengdu (CN); Chunsheng Chen, Chengdu (CN); Ning Chen, Shanghai (CN); Jianxia Wang, Meishan (CN)

(73) Assignees: Chengdu Kuachang Medical Industrial Limited, Chengdu (CN); Chengdu Kuachang Science & Technology Co., Ltd., Chengdu (CN)

( * ) Notice: Subject to any disclaimer, the term of this patent is extended or adjusted under 35 U.S.C. 154(b) by 0 days.

(21) Appl. No.: 11/258,996

(22) Filed: Oct. 27, 2005

(65) Prior Publication Data

US 2006/0057631 A1 Mar. 16, 2006

Related U.S. Application Data

(63) Continuation of application No. PCT/CN2004/000437, filed on Apr. 30, 2004, and a continuation of application No. PCT/CN2004/000077, filed on Jan. 20, 2004, and a continuation of application No. PCT/CN2004/000203, filed on Mar. 15, 2004.

(30) Foreign Application Priority Data

Apr. 30, 2003 (CN) ................................ 03 1 17787

(51) Int. Cl.

| | |
|---|---|
| *G01N 21/00* | (2006.01) |
| *G01N 33/00* | (2006.01) |
| *G01N 33/53* | (2006.01) |
| *G01N 33/543* | (2006.01) |
| *G01N 33/544* | (2006.01) |
| *G01N 33/545* | (2006.01) |
| *G01N 33/546* | (2006.01) |
| *G01N 33/547* | (2006.01) |
| *G01N 33/551* | (2006.01) |
| *G01N 33/552* | (2006.01) |
| *G01N 33/553* | (2006.01) |

(52) U.S. Cl. ..................... 436/524; 422/82.09; 435/7.1; 435/7.92; 435/7.94; 435/288.3; 435/288.4; 436/523; 436/525; 436/526; 436/527; 436/528; 436/529; 436/530; 436/531; 436/164; 977/702; 977/705; 977/773; 977/789; 977/791; 977/792; 977/793; 977/794; 977/795; 977/920; 977/957; 977/958

(58) Field of Classification Search ................. 977/702, 977/705, 773, 789, 791–793; 436/523–531; 435/288.3–288.4

See application file for complete search history.

(56) References Cited

U.S. PATENT DOCUMENTS 5,447,837 A * 9/1995 Urnovitz ........................ 435/5

(Continued)

FOREIGN PATENT DOCUMENTS

WO WO 0000808 A2 * 1/2000

(Continued)

OTHER PUBLICATIONS

Grabar et al., "Preparation and characterization of Au Colloid Monolayers", 1995, Anal. Chem., vol. 67, pp. 735-743.*

(Continued)

*Primary Examiner*—Unsu Jung

(74) *Attorney, Agent, or Firm*—Birch, Stewart, Kolasch & Birch, LLP

(57) ABSTRACT

This invention involves the nano-structured support used for separation or/and analysis, especially the chip substrate, ELISA plate substrate, planar chromatography strip and chromatography gel. Besides, it involves the functionalized nano-structured support of high sensibility for separation or/and analysis, especially the analysis-chip, ELISA plate, planar chromatography reagent strip and chromatography gel. In addition, this invention also involves the nano-structured marking system for analysis. Moreover, it concerns the test kit; especially the chip kit, ELISA kit, and planar chromatography kit. What's more, this invention involves the preparing methods and the applications of all those mentioned above, especially the chip analysis, analyses with ELISA plate, planar chromatography strip and chromatography separation.

Figure 1:
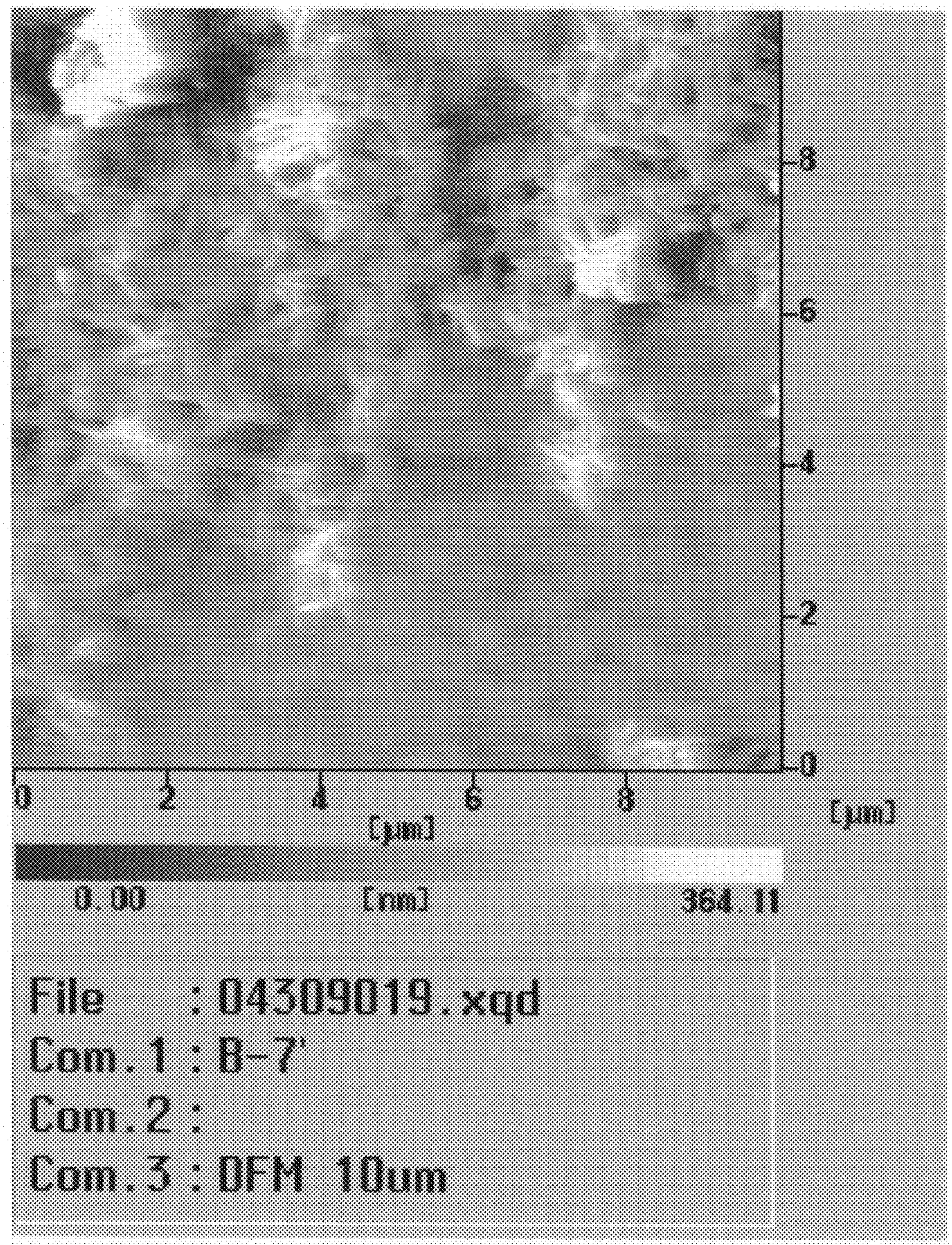

29 Claims, 3 Drawing Sheets
(3 of 3 Drawing Sheet(s) Filed in Color)

U.S. PATENT DOCUMENTS

| | | | | |
|---|---|---|---|---|
| 5,846,708 | A * | 12/1998 | Hollis et al. | 506/12 |
| 6,242,264 | B1 * | 6/2001 | Natan et al. | 436/171 |
| 6,329,209 | B1 * | 12/2001 | Wagner et al. | 436/518 |
| 2001/0029049 | A1 * | 10/2001 | Walt et al. | 436/518 |
| 2002/0081714 | A1 * | 6/2002 | Jain et al. | 435/287.2 |
| 2002/0137072 | A1 * | 9/2002 | Mirkin et al. | 435/6 |
| 2003/0029274 | A1 * | 2/2003 | Natan et al. | 75/741 |
| 2003/0059820 | A1 * | 3/2003 | Vo-Dinh | 435/6 |
| 2003/0077625 | A1 * | 4/2003 | Hutchison | 435/6 |
| 2004/0023046 | A1 * | 2/2004 | Schlottig et al. | 428/469 |
| 2004/0142106 | A1 * | 7/2004 | Mirkin et al. | 427/256 |

FOREIGN PATENT DOCUMENTS

| | | | | |
|---|---|---|---|---|
| WO | WO 0008445 | A1 * | 2/2000 | |
| WO | WO 0183825 | A2 * | 11/2001 | |

OTHER PUBLICATIONS

Qhobosheane et al., "Biochemically functionalized silica nanoparticles", Analyst, 2001, vol. 126, pp. 1274-1278.*

* cited by examiner

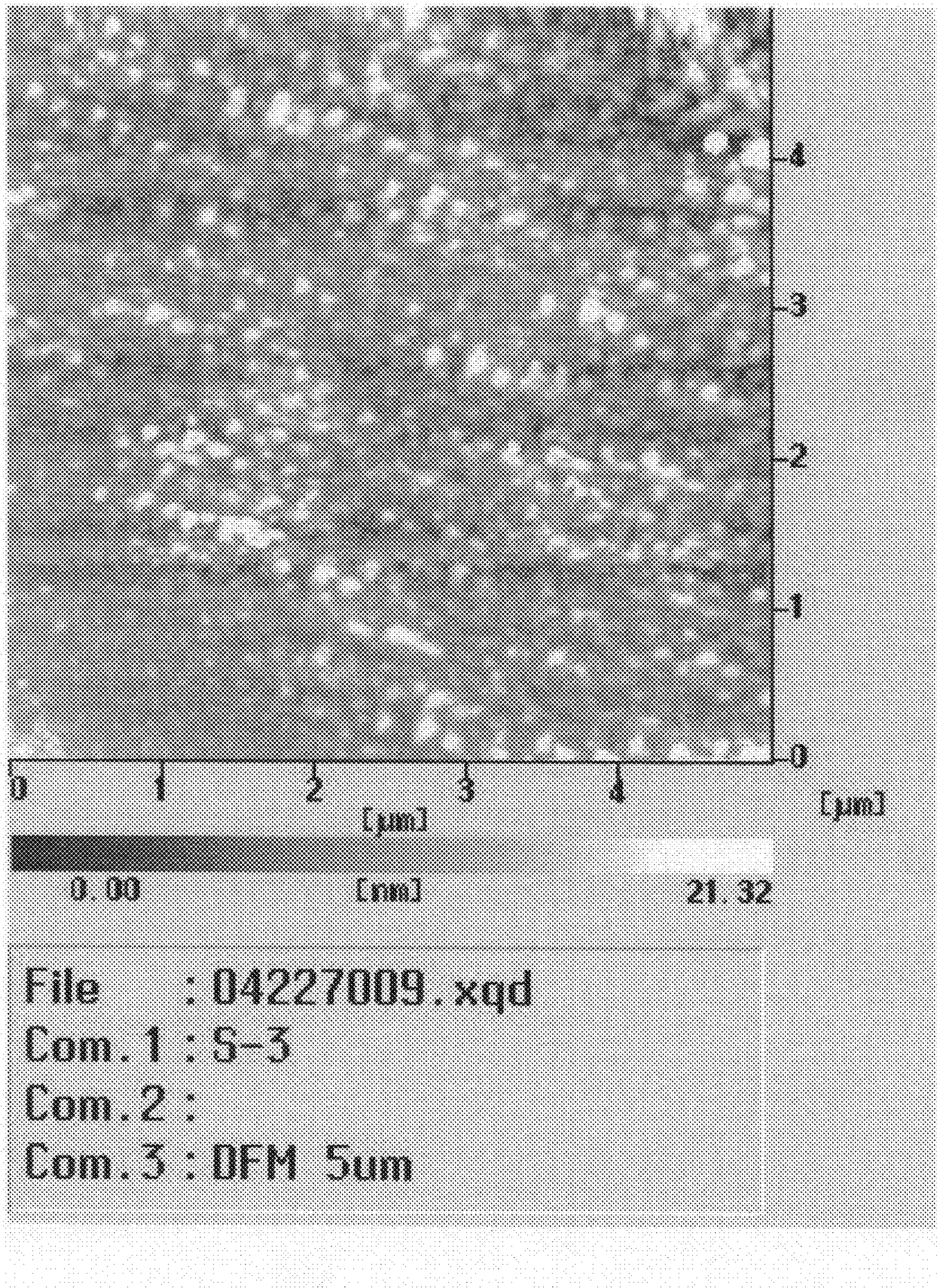
Fig 2-a

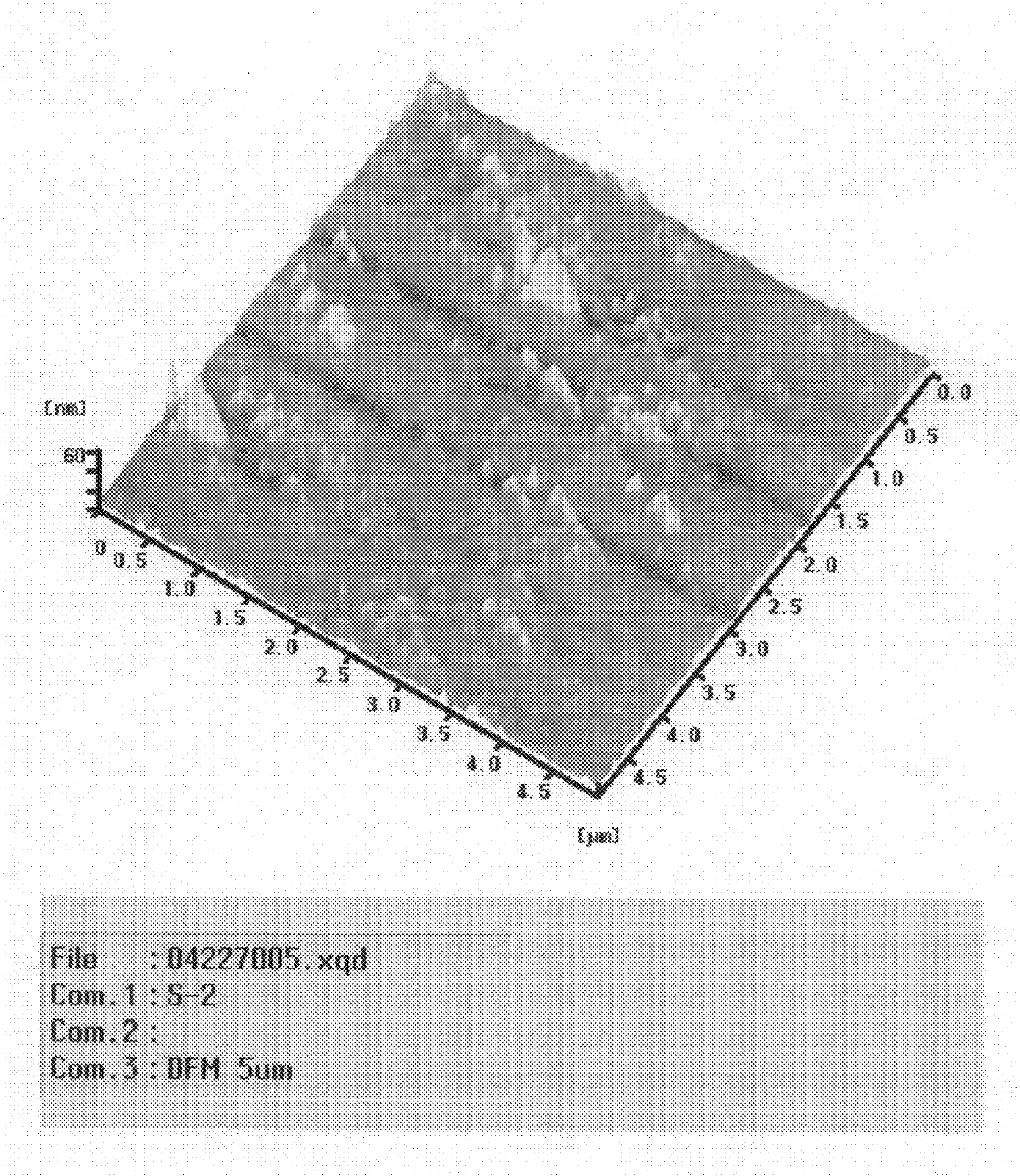
Fig 2-b

NANO-STRUCTURED DEVICE FOR ANALYSIS OR SEPARATION, AND ITS PREPARATION AND APPLICATION

This application is a Continuation of co-pending PCT International Application Nos. PCT/CN2004/000437 filed on Apr. 30, 2004, PCT/CN2004/00077, filed on Jan. 20, 2004, and PCT/CN2004/00203, filed on Mar. 15, 2004, which designated the United States, and on which priority is claimed under 35 U.S.C. §120. This application also claims priority under 35 U.S.C. §119(a) on Patent Application No(s). 03117787.5 filed in China on Apr. 30, 2003. The entire contents of each of the above documents is hereby incorporated by reference.

TECHNICAL FIELD

This invention relates to a nano-structured support, especially nano-structured substrate of analysis-chip, nano-structured substrate of ELISA plate, nano-structured strip of planar chromatography, and nano-structured chromatography gel used in separation or/and analysis. This invention relates to also a functionalized nano-structured support with high sensitivity used in separation or/and analysis, especially nano-structured analysis-chip, nano-structured ELISA plate, nano-structured reagent strip of planar chromatography and nano-structured gel of chromatography. This invention relates to also a marking system with nano-structured used in analysis. Moreover, this invention relates to a kit, especially analysis-chip kit, ELISA kit, and planar chromatography kit. The methods for preparation and the applications thereof, especially in the analysis with analysis-chip, with ELISA plate, with planar chromatography strip and in chromatography separation, are also provided.

TECHNICAL BACKGROUND

Support, especially the functionalized support with selective reactivity has been applied extensively in many fields, especially in the fields of qualitative and/or quantitative analysis, or/and separation of targets in a sample. Affinity chromatography gel is an example of functionalized support whereas the antigen or/and antibody analysis-chip is an example of analysis application.

Most of present functionalized supports are produced by directly immobilizing functional reagent (e.g. probe-ligand) onto the surface of a support. For example, glass derivatives (such as amino-group glass slide, aldehyde-group glass slide, epoxy-group glass slide, polyamino acid-coated glass slide, etc.) are the main substrates used nowadays for analysis-chips. The immobilized functional reagent, produced by immobilizing the functional reagent onto the substrate, is one of the key factors deciding the test sensitivity and specificity of the analysis-chip. The available immobilization measures are mainly covalent bond immobilization, physicochemical adsorption, embedding, and cross-linking. The reaction kinetic condition for functional reagents is to be optimized and detailed, which is manifested as improved sensitivity or/and specificity; or/and to shortened reaction time.

How to improve the immobilized functional reagent through modifying the surface of a support has long been a major problem in R&D for analysis or/and separation, and has attracted many laboratories worldwide. Though many researchers are working on the modification of the support surface by using nano-particles or colloid, they either fail to take the sensitivity as the primary goal (e.g. WO 0183825), or fail to take the immobilized functional reagents as the main goal (e.g. USA Patent Application No. 20030207296), or obtain the support at an extremely high cost (e.g. the aligned nano-structured support by USA 3M Company, U.S. Pat. No. 5,709,943). In the document of WO 0183825, colloid, especially the organic particles at size of 100-500 nm is used, so as to decrease the workload in analysis-chip manufacturing, e.g. the processing procedures are so simplified as to produce analysis-chips with uniform probe spots. In the USA Patent Application No. 20030207296, the emphasis is laid on taking the nano-particle itself as the ligand support in the nucleic acid test. However the research on the modified nano-particle substrate is inadequate.

Another key factor for sensitivity and test time is the marking system. The prevalent marking system today is a molecular dispersion marking system whose sensitivity is yet to be improved, in which many labs are engaged. Some application of nano-particles has been introduced into the present marking systems in order to increase test sensitivity (such as WO 00/72018 A1, U.S. Patent Application No. 20030211488, whose research thereof uses colloidal gold as the labeling reagent, supplemented with silver enhancement system), but these particles are either labeling materials themselves, or reinforcing agents (e.g. U.S. Patent Application No. 20030232388, 20030166207, 20020142480, 20030211488, whose research thereof uses metals with raman enhancement effect). There are some patents wherein some nanometer crystal particles are employed as identifying codes of nano-particle supports, which connect molecules with varied activities (e.g. U.S. Pat. No. 6,544,732).

In addition, functionalized support is used extensively in separating device such as chromatography device, e.g., that comprising affinity chromatography gel. Although the particle employed by the functional matrix of chromatography has larger surface region than substrate, it leaves much to be desired in terms of chromatography time, and rate etc.

DISCLOSURE OF INVENTION

The main objective of this invention is to increase the reaction efficiency of functionalized support or/and marker in analysis or/and separation at relatively lower cost, thereby increasing the test sensitivity or/and shortening the test time or/and providing more kind of supports with adequate sensitivity. The objective is attained through the development of nano-structured support, functionalized nano-structured support and nano-structured marking system of this invention. Based on the nature of the research, i.e. that study of the support and functionalized support, improvement of separation media as well as their efficiency becomes the additional objective of the invention.

So, the first embodiment of this invention provides a nano-structured support used for analysis or/and separation, which comprises nano-structured region, said nano-structured region comprising conventional solid phase support and the fixed nano-structure thereon, said nano-structure comprising non-aligned nano-structure units, said nano-structure units including nano-convex with a height over 3 nm, which cross-section at its half-height presents at least one dimension as 1-500 nm, optimally 1-100 nm, wherein said nano-structured region is characterized by: 1). a distribution density of said nano-convex of more than 1 nano-convex/$\mu m^2$, optimally more than 10 nano-convex/$\mu m^2$; and 2). any one or more of the following characteristics: (1). a nano-structure covering rate of over 20%, optimally more than 30%; (2). a surface-increasing rate of more than 200%, preferably more than 300%, optimally more than 400%; (3). an adsorption-increasing rate of more than 115%, preferably more than 130%, and optimally more than 150%; and (4). an adsorption-attenuating rate of less than 90%, optimally less than 80%.

In this invention, the term “nano-convex” refers to a convex with only one head, at least one of whose three dimensions presents a size of 1-1000 nm, such as a nano-particle fixed on a support or an other structure; the term “nano-structure unit” refers to a structure unit, at least one of whose three dimensions presents a size of 1-1000 nm, such as a nano-particle; the term “nano-structure” refers to a structure with a height of less than 1000 nm, which is composed of nano-structure units. Some examples of the nano-structure are: tree branch, hilllike, net or other geometric figure nano-structures, which comprise nano-structure unit or nano-convex and present the correlation among nano-structure units or nano-convex objects (e.g. the tree branch nano-structure may be upwards or parallel to the surface etc; Diagram 1 will give a illustrated example of these nano-convexes or the branch-shaped objects containing nano-convexes).

In this invention, the term “nano-structured region” refers to an region of the nano-structured support, which presents the characteristics determined by this invention (e.g. the distribution form and the distribution density of nano-structure units in the region, etc.) and comprises the said nano-structure and optionally, the surface of conventional support without the nano-structure fixed thereon; the term “non-nano-structured region” refers to an region on nano-structured support beyond the nano-structured region. Non-nano-stuctured region may contain nano-stuctures but does not presents the characteristics determined by this invention. The nano-structured support of this invention comprises nano-structured region, and optionally non-nano-strctured region. In this invention, the target of the analysis or/and separation includes one or more groups of the following materials: polypeptide, drug interacted with polypeptide (polypeptide-related-drug), nucleic acid, drug interacted with nucleic acid (nucleic acid-related-drug).

In this invention, the term “nano-structure covering rate of the nano-structured region” refers to the percentage of the area of conventional solid phase support covered by the nano-structure in the total area of the conventional solid phase support in the nano-structured region: the nano-structure covering rate of the nano-structured region=the area of the conventional solid phase support covered by nano-stucture/the total area of the conventional solid phase support in the nano-structured region.

In this invention, the term “surface-increasing rate of the nano-structured region” refers to the ratio between the area of the nano-structured region and the area of the conventional solid phase support in the nano-structured region: the surface-increasing rate=(the surface area of the nano-structured region/the surface area of the conventional solid phase support in the nano-structured region)×100%. The rate can be measured directly or indirectly.

In this invention, the term “adsorption-increasing rate of the nano-structured region” refers to a comparison of the adsorption capacity of the nano-structured region with that of the conventional solid phase support used for forming the nano-structured region: the adsorption-increasing rate=(the adsorption capacity of the nano-structured region/the adsorption capacity of the corresponding conventional solid phase support)×100%. The selection of the adsorbed material in measurement goes in accordance with the established method.

In this invention, the term “adsorption-attenuating rate of the nano-structured region” refers to a comparison of the adsorption attenuating velocity of the nano-structured region and that of the conventional support used for forming the nano-structured region, as the target concentration decreases: the adsorption attenuating rate=(the adsorption attenuating velocity of the nano-structured region with the decrease of targets concentration/the adsorption attenuating velocity of the corresponding conventional solid phase support with the decrease of targets concentration)×100%.

The nano-structured support in this invention is of the specific nano-structure features (e.g. the nano-structured region, distribution form and distribution density of nano-structure units therein, covering rate etc.) as well as specific nano-properties (e.g. the surface-increasing rate, absorption-increasing rate, adsorption-attenuating rate, etc.). The nanometer characteristics of the said nano-structured support may or may not be correlated with the said nano-structure.

So, the nano-structured support of this invention differs from the “nano-particle-coated support”. In fact, it is easy for the conventional solid phase support to have nano-particles thereon, as a result of defects in manufacturing, or result of non-technical dust adsorption, etc, but they are not the nano-structured supports of this invention. Though supports can be technically coated with nano-particles, the nano-particle-coated supports attained thereby, in most cases, still do not possess the features of the said invented nano-structured support, especially the features of nano-structured region, (e.g. in terms of the surface increasing rate, adsorption-increasing rate, adsorption attenuating rate etc.). With no distinction from the conventional solid phase support in nature, they are not at all the nano-structured supports of this invention.

The nano-structured support of the invention can be obtained through various preparation methods. However, the preparation method of this invention is an optimized method that places emphasis on an optimized concentration of nano-particle. In an implementation example of the invention, the nano-particle-coated supports, prepared not under the condition of optimized concentration, do not have the features of the said nano-structured supports, so they are not the nano-structured supports of this invention.

In one nano-structured support of this invention, said nano-structure unit is composed of nano-particle with a diameter of 1-500 nm, preferably 1-100 nm, and optimally 1-50 nm. The binding between said nano-particle and support, or/and among the nano-particles can be established through one or more ways, such as: covalent bond linking, non-specific physicochemical adsorption, antigen-antibody adsorption, affinity adsorption, nucleotide coupling conjugation, and heat polymerization below the softening temperature, etc. Optimally, the said binding works through linking agent on the surface of the support or/and nano-particles. The linking agent includes the surface group or/and coating organic.

In one nano-structured support of this invention, said nano-particle includes: 1). inorganic nano-particle including:(1). magnetic nano-particle, and/or (2). non-magnetic inorganic nano-particle including non-magnetic metal and/or non-metal nano-particle; or/and 2). organic nano-particle; or/and 3). derivative of inorganic or/and organic nano-particle, which includes derivative with bound surface group or/and coated organic compound. The said organic nano-particle includes those such as plastic nano-particle, polysaccharide nano-particle, etc.

In one nano-structured support of this invention, said non-magnetic non-metal inorganic nano-particle includes oxide nano-particle, including silicon oxide particle, titanium oxide particle, or/and alumina oxide particle.

In one nano-structured support of this invention, said non-magnetic metal nano-particle includes gold particle, vanadium particle, or/and lead particle.

In one nano-structured support of this invention: 1). said surface group includes one or more of following surface groupes: amino-, aldehyde-, epoxy-, amino diazane, diethylaminoethyl, diethyl-(2-hydroxypropyl) aminoethyl, carboxymethyl, sulfopropyl, mercaptoethylpyridine, siloxanyl, thioalcohol- and alkyl-; and 2). said organic compound includes one or more groups of following substances: (1). surfactant including polyvinylpyrrolidone or/and Tween; (2). polyelectrolyte including polyamino acid; (3). oleophilic compound including polysiloxane; (4). ion exchange polymer including dextran derivative, agarose derivative, cellulose derivative, or/and polyacrylamide; and (5). affinity materials including heparin natrium, antigen or/and antibody.

The surface group could also be long-armed surface group R—(CH2)x-, wherein R stands for the surface group, x is no less than 2, preferably larger than 4, optimally larger than 6. In this invention, the surface group combinable with the surface of nano-particle covers a wide range, particularly because of the preparation of coated derivative. For instance, in implementation examples of the invention, when there is an alkyl-group on the nano-particle derivatives such as super-hydrophobic silica (CS7), the coated derivative is covered by organic compound, such as polyamino acid with amino-groups, amino diazane with amino and amino diazanyl-groups, DEAE-Dextran with diethylaminoethyl, etc.

On the other hand, surfactant like polyvinylpyrrolidine (PVP), polyelectrolyte like polyamino acid, ion exchange polymer like DEAE-Dextran, affinity material like Protein A etc. are applied in this invention for the preparation of ligand/nano-particles/substrate complex and ligand/nano-particle/molecular labeling material complex. In fact, the importance of particle derivative lies in the coated derivative. The coated derivative in the invention can be mono-coated or multi-coated. For example, silica particles are coated with dispersants or/and dispersing stabilizers (simplex coating), then with PVP (duplex coating), and even further with Protein A (triplex coating). Hence, available organic compound is numerous. The surface group or/and organic compound can be fixed on nano-particlse or/and conventional supports.

One nano-structured support of this invention, said conventional solid phase support presents a sizes over 1000 nm and is made of one or more groups of following materials or their derivatives: glass, silica, silica gel, ceramics, metallic oxide, metal, polymer material and their complexes, wherein said derivative includes those derived surficially with surface groups or/and coated organic compounds. The said conventional supports include the planar support (e.g. the substrate of analysis-chip, ELISA plate, etc), granular support (e.g. the chromatography gel, especially micrometer particle chromatography gel) and membranous support (e.g. plane chromatography strip).

One nano-structured support of this invention includes: 1). nano-particle/substrate complex; 2). nano-particle/micro-particle complex; or 3). nano-particle/micro-particle/substrate complex. What is to be emphasized is that the invented nano-particle/substrate complex, nano-particle/micrometer particle complex or nano-particle/micrometer particle/substrate complex is used as those of the invented nano-structured support.

One nano-structured support of this invention includes: 1). nano-structured substrate for analysis-chip; 2). nano-structured microwell plate for Elisa; 3). nano-structured substrate for planar chromatography; 4). nano-structured matrix for separation; or 5). nano-structured matrix for separation, including nano-structured chromatography gel.

The second embodiment of this invention provides a method for preparing the nano-structured support of the first embodiment of this invention, comprising: 1). contacting suspension of said nano-particle and said conventional solid phase support; and 2). fixing said nano-particle on said conventional solid phase support, wherein said suspension presents a concentration of from 1/500 to 1/150000 g/ml in nano-particle weight/volume concentration, or from 0.12 to 37.4 nmol in nano-particle mole concentration. To have a definited nano-particle concentration is one of the key factors in the method of this invention.

In one method of the second embodiment of this invention, said concentration is from 1/5000 to 1/150000 g/ml in nano-particle weight/volume concentration, or from 0.12 to 3.74 nmol in nano-particle mole concentration. In one method of the second embodiment of this invention, said concentration is 1/20000 to 1/60000 g/ml in nano-particle weight/volume concentration or from 0.31 to 0.93 nmol in nano-particle mole concentration.

One method of the second embodiment of this invention comprises also one or more of the following activation treatmens: 1) activating said nano-particle or/and conventional solid phase support firstly, then conducting said contacting and fixing; 2) conducting said contacting and fixing firstly, then activating said nano-particle or/and conventional solid phase support; 3) activating said nano-particle or/and conventional solid phase support firstly, conducting said contacting and fixing, and then re-activating said nano-particle or/and conventional solid phase support again; wherein: said activation includes introduction of said surface group or/and organic compound on the surface.

One method of the second embodiment of this invention comprises also a chemical cross-linking treatment after said fixing. Cross-linking agent usable in the invention includes coupling agent, such as epoxy chloropropane, urotropine, etc.

One method of the second embodiment of this invention comprises also, after said fixing, a heat treatment comprising heating and sequent cooling, wherein said heating is processed at over 30° C., preferably at over 37° C., optimally at over 40° C., but at below sintering point of said conventional solid phase support. In existing techniques, one of the measures to improve the stability of nano-particle-coated substrates lies in the heat treatment of the support sintering point. However, heating at the sintering point tends to bring about deformation of the support, causing difficulties in application. Surprisingly enough, though the heat treatment in this invention is conducted at the temperature a dozen or even a hundred degrees below the sintering point, it is still able to create a strong bonding between the support and nano-particles. This invention is not intended to discuss the theory beyond the assumption that nano-particles may possess heat characteristics different from other conventional materials. The heat treatment method of this invention will cause no deformation of supports.

The third embodiment of this invention provides a functionalized nano-structured support for analysis or/and separation, which comprises functionalized nano-structured region, said functionalized nano-structured region comprising conventional solid phase support and the fixed functionalized nano-structure thereon, said functionalized nano-structure comprising non-aligned nano-structure units and functional reagent bound thereon, said functionalized nano-structure unit including nano-convex with a height over 3 nm, which cross-section at its half-height presents at least one dimension as 1-500 nm, optimally 1-100 nm, wherein said functionalized nano-structured region is characterized by: 1). a distribution density of said nano-convex of more than 1 nano-convex/μm$^2$, optimally more than 10 nano-convex/μm$^2$; and 2). any one or more of the following characteristics: (1).

a nano-structure covering rate of more than 30%, optimally more than 75%; (2). a surface-increasing rate of more than 200%, preferably more than 400%, optimally more than 600%; (3). an adsorption-increasing rate of more than 115%, preferably more than 130%, optimally more than 150%; (4). a sensibility-increasing rate of more than 120%, preferably more than 150%, optimally more than 200%; (5). a ratio of signal-attenuated rates of less than 90%, optimally less than 70%; and (6). a ratio of adsorption-attenuated rates of less than 90%, optimally less than 80%.

In this invention, the term "functionalized region" refers to the region on which the said functional reagent is immobilized. It can comprise the complete support or one or several mutually independent regions of the support (e.g. micro-array analysis-chip); the term "non-functionalized region" refers to region other than the functionalized region on the support; the term "functionalized nano-structured region" refers to the region inside the functionalized region, which not only contains the above mentioned functional reagent, but also possesses the characteristics (e.g. the distribution of nano-structure units and distribution density etc) of this invention. It includes the said nano-structure, functional reagent fixed on the nano-structure and optionally existent surface of the conventional solid phase support without the fixed nano-strucuture mentioned-above (in Picture 2, these nano-convex or the tree branch shaped nano-structure could be seen).

In this invention, the term "nano-structured analysis-chip" refers to an analysis-chip that contains at least one said functionalized nano-structured region (e.g. one spot with the functionalized nano-structure on a micro-array analysis-chip). Such an analysis-chip may have several reactors, in which at least one reactor may contain multi-spots with functional reagents (probe spots). If one spot is the functionalized nano-structured region defined by this invention, the whole analysis-chip will be regarded as the functionalized nano-structured support or nano-structured analysis-chip of this invention.

In this invention, the term "functionalized non-nano-structured region" refers to functionalized region other than the functionalized nano-structured region. It may contain nano-structure but does not have the features of functionalized nano-structured region of this invention. The terms "nano-convex", "nano-structure unit", "nano-structure", "nano-structured region", "non-nano-structured region" have been defined in the above paragraphs. The functionalized nano-structured support includes functionalized region and optionally existent non-functionalized region. The functionalized region includes functionalized nano-structured region and optionally existent functionalized non-nano-structured region. In the invention, the functional reagent is that endowed with the said functionalized nano-structured support with reactivity (e.g. the reactivity with target), such as ion exchanger, drug, polypeptide, polysaccharide, vitamin, antibiotic, functional organic, antigen, and viruse, cell or their composition. The functionalized nano-structured support in this invention does not contain labeling material (e.g. the analysis-chip without fluorescein), for it is used in reactors only.

In this invention, the term "nano-structure covering rate of the functionalized nano-structured region" refers to the percentage of the area of conventional solid phase support covered by the nano-structure in the total area of the conventional support in the functionalized nano-structured region: the nano-structure covering rate of the functionalized nano-structured region=the area of the conventional support covered by nano-stucture/the total area of the conventional solid phase support in the functionalized nano-structured region.

In this invention, the term "surface-increasing rate of the functionalized nano-structured region" refers to the ratio between the area of the functionalized nano-structured region and the area of the conventional solid phase support in the functionalized nano-structured region: the surface-increasing rate=(the surface area of the functionalized nano-structured region/the surface area of the conventional solid phase support in the functionalized nano-structured region)×100%. The surface-increasing rate of the functionalized nano-structured region can be measured directly or indirectly. In one of the implementation of the invention, the surface increasing rate of the functionalized nano-structured region of an analysis-chip is measured indirectly by coating the functionalized nano-particle and functional reagent respectively on the whole substrate. The surface-increasing rate in the invented analysis-chip is up to 800% or more.

In this invention, the term "corresponding non nano-structured functionalized support" refers to functionalized support which does not presents the functionalized nano-structured region of this invention but presents the same conventional solid phase support and functional reagent. An example of the non nano-structured functionalized support is the analysis-chip prepared by loading HCV antigens onto epoxy-group glass slides, whereas an example of the functionalized nano-structured support is the analysis-chip of the invention prepared by loading the suspension of HCV antigen-coated silicon oxide nano-particle onto epoxy-group glass slide.

In this invention, the term "sensibility-increasing rate of the functionalized nano-structured region" of this invention refers to a comparison of analytical sensitivities between the functionalized nano-structured region and the non nano-structured functionalized support which possesses the same conventional solid phase support and functional reagent: sensibility-increasing rate=(the sensitivity of the functionalized nano-structured region/the sensitivity of the corresponding non nano-structured functionalized support)×100%.

In this invention, the term "adsorption-increasing rate of the functionalized nano-structured region" refers to a comparison of the adsorption capacities between the functionalized nano-structured region and the non nano-structured functionalized support which possesses the same conventional solid phase support and functional reagent: the adsorption-increasing rate=(the adsorption capacity of the functionalized nano-structured region/the adsorption capacity of the corresponding non nano-structured functionalized support)×100%. In the measurement of adsorption capacity, the selection of the adsorbed material depends on the immobilized functional reagent. The sensitivity-increasing rate of the invented analysis-chip is up to 300% or more.

In this invention, the term "signal-attenuated rate in the functionalized nano-structured region" refers to a comparison between the attenuating velocities of signal identification of the functionalized nano-structured region and that of the non nano-structured functionalized support which possesses the same conventional solid phase support and functional reagent: the signal-attenuated rate=(the attenuating velocity of signal identification of the functionalized nano-structured region with the decrease of targets concentration/the attenuating velocity of signal identification of the corresponding non nano-structured functionalized support with the decrease of targets concentration)×100%.

In this invention, the term "adsorption attenuating rate of the functionalized nano-structured region" refers to a comparison between the adsorption attenuating velocities of the functionalized nano-structured region and that of the non nano-structured functionalized support which possesses the same conventional solid phase support and functional reagent: the adsorption attenuating rate=(the adsorption attenuating velocity of the functionalized nano-structured region with the decrease of targets concentration/the adsorption attenuating velocity of the corresponding non nano-structured functionalized support with the decrease of targets concentration)×100%.

The functionalized nano-structured support of this invention differs from the support with functionalized nano-structure, which is described in PCT International Patent Application PCT/US96/04485 in its technical design. The nano-structure of latter is composed of aligned nano-whiskers. Its optimal preparation also differs from that of this invention. Consequently, it is of high cost, and not able to fix functionalized nano-particle array, as the analysis-chip of this invention does, onto places of the support as required. The functionalized nano-structured support of this invention differ also from other well-known supports with functionalized nano-structure, which do not possesse the specific nano-structure features (e.g. the distribution and distribution density of the functionalized nano-structured regions and nano-structure units therein, the covering rate of nano-structure etc.) as well as specific nanometer properties (e.g. the surface increasing rate, adsorption-increasing rate, adsorption attenuating rate, sensibility-increasing rate, attenuation rate of signal identification, etc.) of the functionalized nano-structured support of this invention.

The nanomter properties in the functionalized nano-structured support of this invention may be related to the nano-structures described above, or the nano-structures not mentioned yet. The functionalized nano-structured support of the invention, with the specific features of nano-structure and properties of nanometer, is as different from "nano-particle-coated supports containing functional reagents" as from "nano-particle-coated supports" in a general sense.

One thing to be specially emphasized is that it is the specific features of nano-structure and the property of nanometer that make the invented functionalized nano-structured support different from functionalized support with nano-particle in general. Though the functionalized support in some literatures (such as No. 20030207296 of USA Patent Application) is the one with the functionalized support and nano-particles thereon, surprisingly we have found from a great many experiments that functionalized supports with different features (e.g. varied appearances) present absolutely different activities (e.g. test sensitivity). The functionalized nano-structured support of this invention has specific features, thereby possessing definite high activity (e.g. test sensitivity). In addition, the Self-assemble metal colloid monolayers claimed by U.S. Pat. No. 6,025,202 of USA Patent differ radically from the invented nano-structured support in the technical design. It does not have the features of functionalized nano-structured support of this invention. Actually, functionalized nano-particles affixed on the surface of supports will not necessarily form the functionalized nano-structured region of this invention.

The functionalized nano-structured support of this invention can be obtained via various approaches, but the said method of its preparation is an optimal method. In this preparation, one thing needs to be emphasized: an optimal concentration of functionalized nano-particle is one of the keys for obtaining the functionalized nano-structured supports of this invention. In an implementation example of this invention, the nano-particle-coated functionalized supports prepared not under the said optimal concentration condition, do not have the features of the functionalized nano-structured support, so they are not the invented functionalized nano-structured supports. We will discuss and explore the differences, like that in appearance in an implementation example. With the help of electronic probe microscope (DFM) and electronic scanning microscope, the observed convex object whose size is far bigger than that of nanometer may be nano-particle aggregates. Furthermore, large-sized nano-particle aggregates may lose or partially lose features of nano-structures at least. For example, we found in the implementation examples that the functionalized support is generated when the concentration of active silica is over 1%, wherein this kind of convex object (functionalized n non-ano-structured region) has a much larger proportion in the functionalized region, therefore, presenting a much lower test sensitivity.

In conclusion, the supports with functionalized nano-particles generated without strict structural design are different from the functionalized nano-structured support of this invention, which presents the features described above. Additionally, the invented functionalized nano-structured support includes simplex functionalized nano-structured support and multiplex functionalized nano-structured support, wherein the said simplex functionalized nano-structured support is made by fixing the functionalized nano-particle containing only one type of functional reagent onto an functionalized support; whereas, the multiplex functionalized nano-structured support is made by fixzing the functionalized nano-particle containing more than two types of functional reagents onto an functionalized support. A analysis-chip and a planar chromatography reagent strip are the examples of device containing multiplex functionalized nano-structured support; whereas an ELISA plate is the example of device containing simplex functionalized nano-structured support. In No. 20030207296 USA Patent Application, the support is only a support with simplex functionalized nano-structure.

In one functionalized nano-structured support of this invention, said separation or/and analysis includes polypeptide or/and polypeptide-related-drug separation or/and analysis. It is well known that there are many functional reagents that can react with target polypeptides, ion exchangers, drugs, polypeptides, polysaccharides, vitamins, antibiotics, functional organics, antigens, and viruses, cells or their compositions as some of the examples. In this type of functionalized nano-structured supports, the functionalized nano-structure could be bound to the support not through nucleotide coupling conjugation, but by one or several approaches mentioned below: covalent bond linking, nonspecific physico-chemical adsorption, antigen-antibody adsorption, and affinity adsorption. And the bonding is completed with the help of the linking agent on the surface of supports or/and nano-particles. The linking agents include surface groups, organic compounds or/and the functional reagent. In No. 20030207296 USA Patent Application, the bonding of nano-particles and substrates must depend on nucleic acid coupling effect, so it is unsuitable for detecting and separating other materials, except nucleic acids like polypeptides.

In one functionalized nano-structured support of this invention, said separation or/and analysis includes nucleic acid or/and nucleic acid-related-drug separation or/and analysis. The nucleic acid nano-particle-coated substrate of this invention differs from that claimed by No. 20030207296 USA patent application, because the former is of the specific feature of nano-structures and properties of nanometer.

One functionalized nano-structured support of this invention is a complex of functionalized nano-particle and support, wherein: 1). said functionalized nano-particle comprises: (1). nano-particle with a diameter of 1-500 nm, preferably 1-100 nm, and optimally 1-50 nm, and one or more said functional reagents immobilized thereon; and optionally (2). linking agent; 2). said support is a conventional solid phase support, or the nano-structured support in the first embodiment of this invention.

In one functionalized nano-structured support of this invention, said nano-particle includes that described in the first embodiment of this invention, optimally the non-magnetic non-metal inorganic nano-particle and/or its derivative. Moreover, its structural features are different from those described in U.S. Pat. No. 6,025,202 and PCT international patent application PCT/US96/004485. Besides, its optimal design also includes the functionalized nano-structured support without metal surfaces and metal nano-particles, whereas in U.S. Pat. No. 6,025,202, the surface of nano-struture is coated with metal, and in PCT international patent application PCT/US96/004485 colloid gold is employed (colloid gold is fixed on organic membrane, while the organic membrane is fixed on substrate). Therefore the manufacture of the functionalized nano-structured support of this invention is simpler and the cost is lower.

One functionalized nano-structured support of this invention includes: 1). functionalized nano-particle/substrate complex; 2). functionalized nano-particle/micro-particle complex; 3). functionalized nano-particle/nano-structured substrate complex; 4). functionalized nano-particle/nano-structured micro-particle complex; or 5). any combination from above complex.

One functionalized nano-structured support of this invention includes: 1). functional reagent/nano-structured substrate complex; 2). functional reagent/nano-structured micro-particle complex; or 3). any combination from above complexes. One functionalized nano-structured support of this invention includes the complex of functional reagent and the nano-structured support in the first embodiment of this invention.

In One functionalized nano-structured support of this invention, there are simplex or multiplex probe-ligands between one or more types of the nano-particles and the support, or/and simplex or multiplex nano-particles between one or more types of the probe-ligands and the support, or/and at least simplex or multiplex probe-ligands between simplex nano-particles and other simplex nano-particles. The functionalized nano-structured support with multiplex probe-ligands between one or several types of nano-particles and support is prepared as such: simplex ligand① is used to coat the support to create ligand①-coated support, simplex ligand ② is used to the coat nano-particle to create the complex of ligand ②/nano-particle(coupling reaction may occur between ligand ① and ligand ②), and then the complex of ligand ②/nano-particle is used to coat or is loaded onto ligand①-coated support to create the complex of ligand②-nano-particle-ligand②-ligand①-support. When the layer of probe-ligand is more than 2, similar method will be adopted. There are many types of functionalized nano-structured supports with multiplex ligands between the simplex nano-particle and other simplex nano-particle, e.g. ligand③-nano-particle-ligand③-ligand②-nano-particle-ligand②-ligand ①-support or ligand ②-nano-particle-ligand②-ligand①-nano-particle-ligand ①- support, etc. There are functionalized nano-structured supports containing multiplex nano-particle between one or several types of ligands, and the support can be prepared as such: first combine one or more types of the nano-particles with above mentioned ligands to form several types of functionalized nano-particles (e.g. ligand ②-nano-particle-ligand, ligand③-nano-particle-ligand②, ligand①-nano- particle-ligand①, etc.), and then these functionalized nano-particles are bound to the supports successively or simultaneously, yielding functionalized nano-structured supports of ligand②-nano-particle- ligand②- ligand①nano-particle-ligand①-support, ligand③- nano-particle- ligand ②-ligand①-nano- particle- ligand①-support, etc.

One functionalized nano-structured support of this invention includes nano-structured analysis-chip.

One functionalized nano-structured support of this invention includes 1). nano-structured ELSA plate; 2). nano-structured planar-chromatography strip; or 3). functionalized nano-structured matrix for separation, including functionalized nano-structured chromatography gel.

The fourth embodiment of this invention provides a method of preparing said functionalized nano-structured support of this invention, comprising: 1). contacting suspension of said functionalized nano-particle and said conventional solid phase support; and 2). fixing said functionalized nano-particle on said conventional solid phase support, wherein: said suspension presents a concentration of from 1/500 to 1/150000 g/ml in nano-particle weight/volume concentration, or from 0.12 to 37.4 nmol in nano-particle mole concentration; said contacting refers to point-contact whose contact diameter is less than 0.5 mm, or surface-contact whose contact diameter is more than 0.5 mm. The following is an example of forming the invented complex of the functionalized nano-particle and the support: nano-particle suspension is mixed and reacted with probe-ligand solution to generate functionalized nano-particle, and then the mixed solution is spotted onto the substrate of substrates on analysis-chip to have binding reaction etc.

The functionalized nano-structured support of this invention can also be prepared through methods shared with other structures, e.g. the substrate with multi-wells etc. The said functionalized nano-particle could be prepared by mixing nano-particle and probe-ligands with other materials, e.g. nano-particle suspension containing colorants or/and adhesives, probe-ligand solution containing stabilizers, etc. The said suspension of functionalized nano-particles includes the mixture (e.g. unpurified products after the mixing reaction between nano-particle and probe-ligand) and purified substance (e.g. the purified products free of probe-ligand by centrifugal separation after the mixing reaction between nano-particle and probe-ligand), and on one type of nano-particles in the purified substance, one or several types of probe-ligands are immobilized. One thing that is to be emphasized particularly is: when nano-particles are either under or over diluted, the said complex prepared from the nano-particles will present no increase of sensitivity.

In one method of the fourth embodiment of this invention, said concentration is from 1/5000 to 1/150000 g/ml in nano-particle weight/volume concentration, or from 0.12 to 3.74 nmol in nano-particle mole concentration.

In one method of the fourth embodiment of this invention, said concentration is from 1/20000 to 1/60000 g/ml in nano-particle weight/volume concentration, or from 0.31 to 0.93 nmol in nano-particle mole concentration.

One method of the fourth embodiment of this invention comprises also a chemical cross-linking after said fixing.

One method of the fourth embodiment of this invention comprises also, after said fixing, a heat treatment comprising heating and sequent cooling, wherein said heating is processed at over 30° C., preferably at over 37° C., optimally at over 40° C., but at below sintering point of the said support, with or without the protection of functional reagent protectant and the subsequent cooling. The said functional reagent includes one or more of stabilizers: amino acid, protein and sugar.

The fifth embodiment of this invention provides a device for analysis or/and separation, comprising the functionalized nano-structured support of this invention, or/and the nano-structured support of this invention. A device of this invention includes the device used for polypeptide or/and polypeptide-related drug analyses. A device of this invention includes the device used for nucleic acid or/and nucleic acid-related drug analysis. The invented functionalized nano-structured support can be used as analysis-chip, ELISA plate, planar chromatography reagent strip, chromatography gel and their assembled devices.

One device of this invention includes: 1). analysis-chip with microarray; or 2). analysis-chip with microarray and channel; or 3). analysis-chip with channel, wherein said channel includes: (i). nano-structured channel comprising said nano-structured support; or/and (ii). functionalized nano-structured channel comprising said functionalized nano-structured support. An important device of this invention is the invented analysis-chip.

One of the invented analysis-chips is the analysis-chip with channels. At present, the microchannel or microflowing path is the most widely studied subject among all the reactor channel structures and reactor separating structures. The size of microchannel in general is less than 0.10 mm in width, and less than 0.025 mm in depth, therefore a concave channel. The analysis-chip with microchannels has been called microchannelled analysis-chip; that is a miniature of a comprehensive analytic system which employs microchannels as the network to connect micropump, microvalve, microvessel, microelectrode, microanalysis units etc. so that it can combine sampling, pre-processing, liquid-delivering and other test functions into one.

Generally, in every reactor of microchanneled analysis-chip, only one type of probe-ligand is immobilized, with only one target in the sample detected at one test. An example for microchanneled analysis-chip is the analysis-chip of Caliper Technologies Inc. (www.caliper.com). The strength of microchannel analysis-chip is its high sensitivity and fast speed. The weakness is: 1) in the process of manufacturing, the microchannel should be etched beforehand. Then probe is deposited thereon. After that, the microchannel is enclosed. Owing to its complicated structure, industralization is difficult; 2) during the detection, the flowing speed of liquid requires some sophisticated instruments, e.g. electronic osmosis device and etc.; 3) after reaction, some test results such as in fluorescence-labeled detection, cannot be read directly by a common analysis-chip scanner, for the probe molecules are fixed on the inner surface.

Although there are many studies concerning the microchannel analysis-chip recently (No. 878437, 801390 and 090840 in USA Patent Application), the analysis-chip with a channel structure that can be easily manufactured at low cost is still one of heated topics in analysis-chip development. This invented channel is produced through immobilizing nano-structures or/and functionalized nano-structures onto the support. For instance, nano-particles or/and functionalized nano-particles are employed to form a coating in the position of channel on the substrate. Thus dimensions of the channel can be easily controlled, e.g. a microchannel or a wider channel can be formed. Besides, since the nano-particles can be transformed as required, the channel is endowed with the capacity of delivering the flowing phase. Moreover, the cost for manufacture is very low.

One device of this invention comprises ELSA plate, or planar-chromatography strip, or device comprising separation matrix, including chromatography column.

The sixth embodiment of this invention provides a marking system for quantitative or/and qualitative analysis, comprising at least one marker which is a complex of marking-ligand, nano-structure, and molecular labeling reagent, said nano-structure including nano-particle or/and structure consisting of nano-particle, said nano-particle referring to non-magnetic non-metal inorganic particle which presents a diameter of 1-100 nm and itself is not enhancing agent of said labeling reagent.

The marker of this invention, the ligand/nano-particle/molecular labeling material complex, can be either a mixture or purified substance. The purified substance contains one or more molecular labeling materials, one or more types of nano-particle, one or more marking-ligands and optionally, blocking agent. With the invented marker, a wide range of targets can be marked, such as polypeptide or/and polypeptide-related-drug. The invented marker can mark also nucleic acids or/and nucleic acid-related-drug. The marking-ligand used in the marker binds itself to target to realize the function, e.g.: antigen, antibody, single-stranded or multi-stranded DNA, RNA, nucleotide, as well as viruse, cell or their composition etc. In this aspect, the ligand/nano-particle/molecular labeling material complex of this invention is different from ligand-nano-particle complex. Since the labeling material in the invented complex is a molecular labeling material (such as Rhodamine) rather than nano-particles, then nano particles are supports rather than labeling material; the support can be employed as one of means for preserving some active sites of marking-ligand.

The ligand/nano-particle/molecular labeling material complex of this invention also differs from ligand-microsphere-fluorescent complex, molecular labeling material-micrometer particle ligand complex, for the support in the invented complex is nano-particle (e.g. nanometer silica), rather than microsphere or microparticle. Nano-particle usually has much higher dispersity and binding activity.

In the marking system of this invention, there are many methods for preparing the lignd/nano-structure/molecular labeling material complex. For example, combine one or several types of the ligands, one or several types of nano-particles, and one or several types of the molecular labeling material in accordance with the following patterns: the probe-ligand is bound with the nano-particle and then to the molecular labeling material; the nano-particle is bound with the molecular labeling material and then to the probe-ligand; the probe-ligand is bound with the molecular labeling material and then to the nano-particle; the probe-ligand is bound with the molecular labeling material and the nano-particle concurrently, as well as other ways based on the above combinations. The method of preparing the invented complex is simple and the produced complex is of good water-solubility and high sensitivity.

In one marking system of this invention, said non-magnetic non-metal inorganic particle includes oxide nano-particle, including silicon oxide particle, titanium oxide particle, or/and alumina oxide particle. In the marking system of this invention, the non-magnetic inorganic non-metal particle includes the non-magnetic inorganic non-metal particle described in the nano-structure considered the primary facet of this invention. In the marking system of the invention, the non-magnetic inorganic non-metallic particles contained in the complex include oxide particles with a size 1-100 nm, optimally 1-50 nm, as well as the derivatives thereof. The oxide particles include silica, titanium dioxide, and alumina. The derivatives include derivatives containing surface group or/and organic compound on the surface. The surface groups include one or more of the following: amino-groups, aldehyde-groups, epoxy-groups, amino diazane, diethylaminoethyl, diethyl- (2-hydroxypropyl) aminoethyl, carboxymethyl, sulfopropyl, mercaptoethylpyridine, siloxanyl, thioalcohol and alkyl-groups. The organic compound includes one or more of the following: surfactants including the types of polyvinylpyrrolidone and TWEEN (polyoxyethylene nonionic detergent), polyelectrolyte including polyamino acid, oleophilic organisms including polysiloxane, ion exchange polymers including dextran derivative, agarose derivative, cellulose derivative, polyacrylamide, and active materials including heparin natrium. The said microcarrier in the microcarrier-coated derivative includes the nano-particle described above.

In one marking system of this invention, said molecular labeling reagent includes one or more of the following materials: fluorescent material, chemiluminescent material, chemiluminescent catalyst, non-ferrous metal salts, dye and pigment, such as one of several materials below: fluorescein, Rhodamine, alga protein, silver salt, enzyme, basic black, basic violet, amino black, Coomassie blue, crystal violet and etc.

The seventh embodiment of this invention provides a method for quantitative or/and qualitative analysis, comprising: 1). capturing, or/and delivering, or/and separating sample target by the device of this invention; and 2). marking the result of 1) with the marking system of this invention. This method involves at least: employment of the functionalized nano-structured support to immobilize the target and employment of the ligand/nano-particle/molecular labeling material complex to mark target; or/and, employment of the nano-structured channel, or/and functionalized nano-structured channel to deliver, or/and separate the reaction media. The immobilizing and marking of targets could be carried out in at least 2 ways: 1) after possible targets in a sample are immobilized in the above-described device, the marker is used to mark the targets which have been bound onto the said functionalized nano-structured support; or, 2) after possible targets in a sample are bound with the marker, the combination is fixed in the device. Moreover, in the implementation examples of the invention, the test sensitivity improves with the increase of nano-particle concentration in the marking-ligand/nano-structure/molecular labeling material complex, which differs totally from the nano-particle effect observed in the said method of preparing functionalized nano-structured support. Therefore, the nano-particle weight/volume concentration (g/ml) in the complex of marking-ligand/nano-structure/molecular labeling material herein is over 1/30000, preferably over 1/1000, and optimally over 1/100, or nano-particle mole concentration is higher than 0.25 nmol, preferably higher than 7.48 nmol, and optimally higher than 74.8 nmol.

The eighth embodiment of this invention provides a kit for quantitative or/and qualitative analysis, comprising: 1). the device of this invention; and 2). marking the result of 1) with the marking system of this invention. The detailed description of the device and the marking system can refer to the related paragraphs above.

One kit of the eighth embodiment of this invention refers to a kit used for polypeptide or/and polypeptide-related-drug analysis, wherein said kit includes: analysis-chip kit, ELISA kit, or planar-chromatography kit.

One kit of the eighth embodiment of this invention refers to a kit for nucleic acid or/and nucleic acid-related-drug analysis.

The ninth embodiment of this invention provides a method for quantitative or/and qualitative analysis, comprising: capturing, or/and delivering, or/and separating sample target by the device of this invention. This method at least involves the following steps: employment of the functionalized nano-structured support to immobiliz the target; or/and employment of the nano-structured channel, or/and functionalized nano-structured channel to deliver, or/and separate the reaction media. The immobilization of targets could be carried out through at least 2 ways: 1) possible targets in a sample are immobilized into the above-described device; or, 2) the possible targets in a sample are bound with the label, and then the combination is immobilized into the device.

The tenth embodiment of this invention provides a kit for quantitative or/and qualitative analyses, comprising the device of this invention. The detailed description of the device can refer to the related paragraphs above.

One kit of the tenth embodiment of this invention refers to a kit used for polypeptide or/and polypeptide-related-drug analysis, wherein said kit includes: 1). analysis-chip kit, 2). ELISA kit, or 3). planar-chromatography kit.

One kit of the tenth embodiment of this invention refers to a kit for nucleic acid or/and nucleic acid-related-drug analysis.

The eleventh embodiment of this invention provides a method for quantitative or/and qualitative analysis, comprising: marking the analysis reaction with the marking system of this invention. The method at least involves employing the marker to mark targets captured by the functionalized support, or adding the marker to a sample to mark possible targets. Besides, in implementation examples about the test method of the invention, the test sensitivity improves with the increase of nano-particle concentration of marking-ligand/nano-structure/molecular labeling material complex, which differs completely from the observed effect of nano-particle in the said method of preparing functionalized nano-structured support. Therefore, the nano-particle weight/volume concentration (g/ml) of the complex of marking-ligand/nano-structured/molecular labeling material is over 1/30000, preferably over 1/1000, and optimally over 1/100, or nano-particle mole concentration is higher than 0.25 nmol, preferably higher than 7.48 nmol, and optimally higher than 74.8 mmol.

The twelfth embodiment of this invention provides a kit for quantitative or/and qualitative analyses, comprising the marking system of this invention. The detailed description of the marking systems can refer to the above relevant paragraphs.

One kit of the twelfth embodiment of this invention refers to a kit used for polypeptide or/and polypeptide-related-drug analysis, wherein said kit includes: 1). analysis-chip kit, 2). ELISA kit, or 3). planar-chromatography kit.

One kit of the twelfth embodiment of this invention refers to a kit for nucleic acid or/and nucleic acid-related-drug analysis.

The thirteenth embodiment of this invention provides a method of testing sample with analysis-chip, comprising: 1). providing respectively: (1). sample which may comprise target; (2). analysis-chip which comprises array of immobilized functional reagent; and (3). marking system which comprises marker, coloring agent, and optionally, coloring-controlling agent and coloring stabilizer, wherein said marker includes complex of marking-ligand, nano-structure, and catalyst, said nano-structure including nano-particle or/and structure consisting of nano-particle, said nano-particle referring to that selected from inorganic particle, or/and organic particle, or/and derivative thereof with a diameter of 1-100 nm, wherein said derivative includes nano-particle with bound surface groups or/and coated organic compounds, said inorganic nano-particle including magnetic inorganic nano-particle and/or non-magnetic inorganic nano-particle, said non-magnetic inorganic nano-particle including non-magnetic metal nano-particle and/or non-magnetic non-metal nano-particle; 2). immobilizing said nano-structure and catalyst of said marker on said analysis-chip, which is performed by: (1). immobilizing said target on said immobilized functional reagent, then immobilizing said marker on said analysis-chip though reaction between said marking-ligand and immobilized target; or (2). fixing said target on partial or total of said marker, then immobilizing said marker on said analysis-chip though reaction between fixed target and said immobilized functional reagent; 3) Adding said coloring agent then conducting coloration on said analysis-chip, wherein: (1). said coloration is performed, with said catalyst immobilized in 2), on said nano-structure fixed in 2) rather than on binding site between said immobilized functional reagent and said target; and (2). said coloring-controlling agent or/and coloring stabilizer are used optionally in said coloration; 4) observing detectable change brought about by said coloration in 3).

The technical design of the method of the thirteenth embodiment of this invention differs from that executing the catalytic reaction at the link of the marking-ligand-captured targets; therefore it is difficult to control the reaction velocity. By contrast, the invented method executes the catalytic reaction on the nano-structure that is bound to the captured targets; therefore it is easy to control the nano-structure parameters (the volume of marking-ligand, the volume of catalyst, the size of nano-particle etc.) and the specificity (such as the tendency of easy separation etc.) so as to control the reaction velocity. As a result, the invented method has faster target-marker reaction time and higher testing ability for specificity.

In one method of the thirteenth embodiment of this invention, said marker also comprises stain, wherein: 1). said stain is used for staining before, or/and in, or/and after said coloration reaction; and 2). said stain is comprised in one or more of the following markers: (1). marking-ligand/nano-structure/catalyst/stain complex; (2). marking-ligand/nano-structure/stain complex; and (3). marking-ligand/stain complex; wherein the nano-structure can be the one described in above facets of the invention. The method of the invention is an optimal design, executing both coloring and dyeing in order to obtain higher sensitivity and specificity.

In one method of the thirteenth embodiment of this invention, said nano-particle in said marking system includes the nano-particle described in the nano-structure considered the first embodiment of this invention.

In one method of the thirteenth embodiment of this invention: 1). said catalyst includes metal catalyst or/and enzyme catalyst used for reduction reaction of metal compound; 2). said stain includes dye; or/and 3). said coloring agent includes metal compound.

The fourteenth embodiment of this invention provides a detecting method with analysis-chip, comprising: 1). providing respectively: (1). sample which may comprise target; (2). analysis-chip which comprises array of immobilized functional reagent; and (3). marking system which comprises marker, coloring agent, and optionally, coloring-controlling agent and coloring stabilizer, said marker comprising marking-ligand, catalyst, stain, and optionally nano-structure, said nano-structure, stain, catalyst and coloring agent; 2) Staining and coloring reaction site in said analysis-chip, though: Adding said sample to said analysis-chip and making said immobilized functional reagent react with said target if any, then adding said marker and coloring agent to said analysis-chip; or Mixing said sample with partial or total said marker, adding the mixture to analysis-chip after said target on said marker though reaction between said target and marking-ligand, and then adding said coloring agent to said analysis-chip after reaction between said immobilized functional reagent and said fixed target; Detecting and analyzing the result of said staining and coloring in 2).

The fifteenth embodiment of this invention provides an analysis-chip kit, comprising at least one making system that is the marking system of this invention.

One kit of the fifteenth embodiment of this invention refers to a kit used for polypeptide or/and polypeptide-related-drug analysis.

One kit of the fifteenth embodiment of this invention refers to a kit used for nucleic acid or/and nucleic acid-related-drug analysis.

The sixteenth embodiment of this invention provides a polypeptide-test method using analysis-chip, comprising at least one of the following procedures using magnetic nano-particle: 1) mixing sample with magnetic nano-particle; 2) mixing sample with complex of functional reagent and magnetic nano-particle; 3) making sample contacting and reacting with nano-structured analysis-chip either with or without external magnetic field, wherein said nano-structure includes magnetic nano-particle; 4). marking reaction using complex of marking-ligand, magnetic nano-particle, molecular labeling material, wherein: (1). said marking is performed either with or without external magnetic field; and (2). said complex comprises one or more molecular labeling reagents, one or more magnetic nano-particles, one or more functional reagents for marking, and optionally blockong agent; wherein: i). said magnetic nano-particle refers to magnetic particle or its derivative, which presents a size of at least one dimension of 1-200 nm, preferably 1-100 nm, optimally 1-50 nm, and furthermore itself is not a enhancer of said molecular labeling material; ii). said marking-ligand is selected from the following materials which interact with the polypeptide: polypeptide, polysaccharide, vitamin, antibiotic, virus, cell and functional organisms; iii). said complex presents, in the marking reaction, a magnetic nano-particle concentration of: (i). more than 1/30000(g/ml), preferably more than 1/3000(g/ml), optimally more than 1/500(g/ml) in nano-particle weight/volum concentration; or (ii). more than 0.25 nmol, preferably more than 2.4 nmol, optimally more than 15.0 nmol in nano-particle mole concentration.

In one method of the sixteenth embodiment of this invention, said magnetic nano-particle is selected from ferrum oxide and its derivative, wherein: 1). said ferrum oxide includes ferrosic oxide or/and ferric sesquioxide; 2). said derivative includes surface-derived derivative with bound surface group or/and coated organic compound. In one method of the sixteenth embodiment of this invention, said external magnetic field is in pulsed wave mode.

The seventeenth embodiment of this invention provides a analysis-chip kit for polypeptide test, comprising said magnetic nano-particle used in the method of the sixteenth embodiment of this invention. See the related paragraphs above for details. In the kit, the magnet nano-particle is used alone to generate the mixture of reaction media; the said ligand/magnetic nano-particle is used to concentrate the sample target, the said complex of ligand/magnetic nano-particle/molecular labeling material is used to mark the reaction. It also includes the use of the separating device considered the fifth facet of the invention.

The eighteenth embodiment of this invention provides a separation method, comprising application of the device of this invention.

The nano-structured support of this invention has advantages of manufacturing simplicity, low cost and good adsorbability.

The method of this invention for preparing the nano-structured support has the following advantages: simplicity, efficacy and low cost, and an obtainable stable nano-structured support with specific features of nano-structure without heating the object up to its sintering point (thus with less change in the support).

The functionalized nano-structured support of this invention has the advantages of high sensitivity, manufacturing simplicity, low cost, high reaction efficiency and high reaction.

The method of this invention for preparing the functionalized nano-structured support has the following advantages: high adaptability, simplicity, efficacy, low cost and an obtainable stable nano-structured support with specific features of nano-structure without heating the object up to its sintering point (thus with less change in the support).

The device of this invention has the advantages of high sensitivity, manufacturing simplicity, low cost, high reaction efficiency and high reaction.

The marking system of this invention has the advantages of high reaction efficiency and simplicity in preparation.

The test method of this invention, which makes use of the functionalized nano-structured support and marking system of this invention, has the following advantages: utilizing both functionalized nano-structured support to capture target polypeptides in the sample, and the complex of ligand/nano-particle/molecular labeling material to mark, which thereby raises greatly the test sensitivity or/and test velocity.

The kit of this invention, containing the functionalized nano-structured support and the marking system of this invention, integrates the merits of both functionalized nano-structured support and the marking system of this invention, and therefore enjoys the high sensitivity, high testing velocity and simple preparation.

The test method of this invention, which makes use of the functionalized nano-structured support of this invention, has the advantages of high sensitivity, high testing velocity and simple preparation. The kit of this invention, which contains the functionalized nano-structured support of this invention, has the advantages of high sensitivity, high testing velocity and simple preparation.

The test method of this invention, which makes use of the marking system of this invention, has the advantages of increased test sensitivity or/and test velocity. The kit of this invention, which contains the marking system of this invention, has the advantages of increased test sensitivity or/and test velocity.

The other test method of this invention has the advantages of increased test sensitivity or/and test velocity. The other kit of this invention has the advantages of increased test sensitivity, velocity and test specificity.

BRIEF DESCRIPTION OF THE ATTACHED PICTURES

The patent or application file contains at least one drawing executed in color. Copies of this patent or patent application publication with color drawing(s) will be provided by the office upon request and payment of the necessary fee.

Picture 1 is a DFM plane figure of a nano-structured support

Picture 2A and 2B are respectively a DFM plane figure and a stereogram of a functionalized nano-structured support.

One thing that needs explanation is these pictures are only few of many DFM plane figures about the nano-structured support and functionalized nano-structured support. Therefore, it cannot be taken as the representative of other nano-structured supports and functionalized nano-structured supports of this invention.

DETAILED DESCRIPTION OF THE INVENTION IMPLEMENTATION

Definition of the Terms

In this invention, the term "device for detection" refers to item containing probe-ligand which is employed to react with target in a sample in the course of quantitative or/and qualitative analyses, e.g. instrument and consumable containing the probe-ligand, and marking kit containg the probe-ligand and the marking-ligand. Cases at concern are analysis-chip, ELISA plate, affinity electrophoresis strip, affinity chromatography column, planar chromatography reagent strip, analysis-chip kit, ELISA plate kit, affinity electrophoresis kit, etc. The course of quantitative or/and qualitative detection can be executed outside the body or inside the body.

In this invention, the term "device for separation" refers to separation necessity containing material with separating function in the course of separation. The course of separation is such that the whole or parts of sample components are obtained via separation methods. Chromatography device is an example for such a device. Chromatography support etc. is an illustration for materials with separating functions.

In this invention, the term "ligand/magnetic nano-particle/solid phase supportcomplex" refers to a complex containing at least ligand, magnetic nano-particles and supports, wherein the ligand, magnetic nano-particles and supports can be combined in various fashions including direct and indirect bindings.

In this invention, the term "functional reagent" refers to material used for capturing the sample target through interaction (such as affinity effect, ion exchange, oleophilic effect, etc.). It includes ligand, and ion exchanger, such as: diethylaminoethyl (DEAE), diethyl-(2-hydroxypropyl) aminoethyl (QAE), carboxymethyl (CM), sulfopropyl (SP), mercaptoethylpyridine (MEP), —NR3+, —RCOOH, siloxanyl, thioalcohol, alkyl group, antigen (Ag), antibody (Ab), ligand, ligation-philic molecule screened by the evolving technology of ligand exponent-enhancing system, ligate, polypeptide, polysaccharide, coenzyme, cofactor, antibiotic, steroid, viruse, cell etc.

In this invention, the term "functional reagent for marking" refers to the material in the marker, used for reacting with the sample target (including affinity effect, ion exchange, oleophilic effect, etc.). The functional reagent for marking including ligand (marking-ligand), such as: antigen (Ag), antibody (Ab), ligand, ligation-philic molecule screened by the evolving technology of ligand exponent-enhancing system, ligate, polypeptides, polysaccharides, coenzymes, cofactors, antibiotics, steroid, viruses, cells etc.

In this invention, the term "polypeptide" includes natural or synthetic proteins, protein fragments, synthetic peptides, etc.; the normal targets in immunoassay and the popular ligands in detection, e.g. antigens, antibodies, etc. all belong to polypeptides.

In this invention, the term "nano-particle" refers to solid particle, which, in three-dimensional space, have at least one-dimensional size less than 500 nm, preferably less than 100 nm, optimally less than 50 nm.

In this invention, the term "solid phase support" includes the conventional support and nano-structured support, wherein said conventional support is the one that has no fixed nano-structure there on the surface; said nano-structured support is the one that has the fixed nano-structure thereon. The solid phase support includes the planar supports (e.g. substrates of biology-chip, ELISA plate etc), granular supports (e.g. the chromatography gel, especially the micrometer particle chromatography gel) and membranous supports (e.g. plane chromatography strip).

In this invention, the term "substrate" refers to the solid phase support containing macroscopical plane with immobilizing function, e.g. the substrate of analysis-chip, the substrate of ELISA plates, electrophoresis gel film, plane chtomatography supports etc.

In this invention, the term "ligand/nano-particle/substrate complex" refers to one kind of composition containing ligand, nano-particles and substrates, whose bonding can be in various forms, such as ligand-nano-particle-substrate, ligand-nano-particle-ligand-substrate, ligand-nano-particle-ligand-nano-particle-substrate, ligand-nano-particle-ligand-nano-particle-ligand-substrate etc.

In this invention, the term "functionalized nano-particle" refers to the complex of functional reagent and nano-particle by the covalence or/and non-covalence bond.

In this invention, the term "reactor" refers to the location (where the specific reaction takes place between the functionalized support and the target molecule,) and other relevant collected structures thereto, such as the reaction-well, relevant partition structure, liquid inlet and outlet in biology chip with open multiple reactor etc., the well on 96-well ELISA plate, reagent strip of rapid test kit etc.

In this invention, the term "base-plate" refers to the product that is based on the substrate, and optionally, combined with other structure (e.g. partition structure), and used for generating the chip after immobilizing the ligand. There are one or several substrate-wells on the base-plate. Usually, there is no partition structure on the single-substrate-well base-plate, which is the substrate in such a case (e.g. amino-group glass slide available on market). There are partition structures on the base-plate of multi-substrate-well; in this case the base-plate includes substrate and partition structure. The substrate-well with immobilized ligand will become a reactor, while the substrate with multi-substrate-well can form a chip with multiple reactors. The substrate is used for immobilizing ligand and other assistants (if required), the chemical and optical properties on its surface are crucial factors to decide the performance and cost of the chip.

In this invention, the term "substrate-well" refers to the structure made up of substrate and the partition structures thereof.

In this invention, the term "analysis-chip", or "chip" in short, refers to a device for analysis for qualitative and/or quantitative analysis (including, but not confined to, analysis-chip microarray or bioarray). In its reactor, the result of specific reaction between the microligand and the sample target molecule can be identified in an addressable way. The core of chip is the reactor thereof, and core of reactor is the substrate of the chip and ligand immobilized thereon. The chip includes microchannel chip (correspond to Microchannel analysis-chip) and microarray chip (correspond to analysis-chip, Microarray, Bioarray), but as known to all it doesn't include existing rapid test strip. The chip in the invention consists of single-reactor or multi-reactors with or without marking system. In the reactor, the distribution density of ligand on the substrate is more than 10 spot/cm$^2$, optimally more than 20 spot/cm$^2$, while the spot area of each ligand spot is not larger than 1 mm$^2$. Featured by its high-throughput and miniaturization, biology-chip have a wide application, including gene expression detection, genes screening, drugs screening, diseases diagnosis and treatment, environment surveillance and contrast, legal identification, etc. Sensitivity and specificity are the two important quality index in biology-chip detection, which, however, is largely determined by the support, especially the functionalized support.

In this invention, the term "functionalized nano-structured chip" refers to a chip which presents at least one said functionalized nano-structured region (e.g. a spot in the probe microarray) of this invention. A chip can have many reactors, and a reactor can have many probe spots that contain functional reagent. If one of the spots is the functionalized nano-structured region of this invention, then the chip is regarded as the functionalized nano-structured support or nano-structured chip of this invention.

In this invention, the term "chromatography" includes affinity chromatography, reversed phase chromatography, hydrophobic chromatography, ion exchange chromatography, etc. It can be classified as planar chromatography (e.g. rapid test strip and rapid test kit) and column chromatography etc.

In this invention, the term "molecular labeling material" refers to material used to generate or help generate the test signal, which are in the form of molecule while labeling, e.g. those commonly used in the chip detection like Rhodamine, CY3 (labeling dye), CY5 (labeling dye) and etc.

In this invention, the term "nano-structure" refers to structure that possess the nanometer size and have partial or complete nanometer effect (e.g. surface effect, size effect).

In this invention, the term "convex height" refers to the distance from top to bottom of a convex object.

In this invention, the term "cross-section at the half-height of the convex" refers to the section which parallels the substrat at the half convex height of the convex.

In this invention, the term "mono-functionalized support" refers to a functionalized support with only one type of said functional reagent immobilized thereon.

In this invention, the term "multi-functionalized support" refers to a functionalized support with several types of (more than one type of) functional reagents immobilized thereon.

In this invention, the term "nano-particle mole concentration" refers to the mole concentration when nano-particles are taken as molecule, which indicates the number of nano-particles in unit volume/liquid. The nano-particle mole concentration in this invention is the weight/volume concentration of nano-particles in the implementation examples of this invention (g/ml)(w/v) (the total weight of nano-particles in unit volume), which is provided by the current suppliers. It is calculated as follows: count the number of nano-particles on the basis of nano-particle concentration, average radius and density, and then take the numbmer as that of molecule into the calculation of the number of nano-particles in unit volume/liquid according to the known formula of mole concentration-weight/volume concentration (g/l).

Following implementation examples will offer more detailed explanations for this invention.

IMPLEMENTATIONS

The nano-particles and the nano-particle derivatives used in the following implementation examples are showed in Table 1.

TABLE 1

| Nano-particle | The size of Nano-particle | Introduced group | Manufacturer |
|---|---|---|---|
| 1. Oxide nano-particle & derivative | | | |
| Silicon oxide nano-particle (STN-3) | 15-25 nm | — | Zhejiang Zhoushan MingRi Nanomaterials Co., Ltd. |
| Silicon oxide(Ludox AS-40) | 30-40 nm | — | Sigma-Aldrich Corp. |
| Titanium oxide nano-particle | <80 nm | — | Zhejiang Zhoushan MingRi Nanomaterials Co., Ltd. |
| Hydrophobic silicon oxide nano-particle (CDS7) | 25-35 nm | Alkyl group | Zhejiang Zhoushan MingRi Nanomaterials Co., Ltd. |
| Metallic nano-particle & derivative | | | |
| Colloidal gold | 20-30 nm | — | Fujiang Quanzhou Changli Biochemical Co., Ltd. |
| Amino colloidal gold (2020) | 1.4 nm | Amino group | American NanoProbes Co. |
| 3. Magnetic nano-particle | | | |
| Water-base magnetic solution (NG-21A) | 10-50 nm | | Mianyang Biyang Magnetic Material Science Co. |

The functional reagents used in the following implementation examples are showed in Table 2.

TABLE 2

| Functional reagent | Type | Source |
|---|---|---|
| EBV-VCA-P18 antigen | Synthetic peptide | Self-prepared* |
| Hepatitis C virus antigen (HCV Ag) | Protein | Institute of Hepatology Beijing university |
| Acquired immunodeficiency syndrome virus antigen (HIV Ag) | Protein | Institute of Hepatology Beijing university |
| Syphilis antigen | Protein | Institute of Hepatology Beijing university |
| Hepatitis B virus surface antibody (HBsAb) | Protein | Institute of Hepatology Beijing university |

*For the preparing method, please refer to Tranchand-Bunel, D., Auriault, C., Diesis, E., Gras-Masse, H. (1998) Detection of human antibodies using "convergent" combinatorial peptide libraries or "mixotopes"designed form a nonvariable antigen: Application to the EBV viral capsid antigen p18, J. Peptide Res. 52, 1998, 495-508.

Substrates and micrometer particles used in the following implementation examples are showed in Table 3.

TABLE 3

| Substrate | Surface polymer | Derivative group | Source |
|---|---|---|---|
| 1. Chip substrate | | | |
| Glass slide | — | — | American TeleChem International, Inc. |
| Amino group glass-slide | — | Amino group | American TeleChem International, Inc. |
| Aldehyde group glass-slide | — | Aldehyde group | American TeleChem International, Inc. |
| Epoxy group glass-slide | — | Epoxy | American TeleChem International, Inc. |
| Amino diazane glass-slide | — | Amino diazane | Self-prepared* |
| PVP-coated glass-slide | PVP | PVP | Self-prepared** |
| DEAE dextran-coated glass-slide | DEAE dextran | DEAE | Self-prepared** |
| Q dextran-coated glass-slide | Q dextran | Q | Self-prepared** |
| 2. The substrate of ELISA plate | | | |
| 96-well polystyrene plate | | | Shenzhen Jincanhua Industrial Co., Ltd. |
| 3. Plane chromatography reagent strip | | | |
| Nitrocellulose film strip | | | Fujiang Quanzhou Changli Biochemical Co., Ltd |
| Nylon cellulose film strip | | | Fujiang Quanzhou Changli Biochemical Co., Ltd |
| 4. micrometer particle | | | |
| Silica gel (particle size of 40-60 μm) | | | Chemical Institute, Chinese Academy of Sciences |
| Sephadex A50 | | | Pharmacis Corp. |

*For the details of the preparing method, refer to Melnyk O et al, Peptide arrays for highly sensitive and special antibody-binding fluorescence arrays, Bioconjug Chem.13: 713-20.2002

**For the details of the preparing method, refer to the patent application of CN03135618.4.

Implementation Example 1

The Preparation of Nano-particle Derivatives

The nano-particle derivatives prepared herein are coated with high polymer with the function of organic compound. Na no-particles employed include those listed in Table 1 (the said nano-particles are all non-crystal nano-particles). Functional polymers employed are listed in Table 4, including polyionic organic compound (polylysine), ionic derivative high polymers (DEAE-dextran, QAE-cellulose, amino diazane-polylysine), and high polymer surfactant (polyvinylpyrrolidone).

The keys points of preparing organic-matter-coated nanoparticles are as follows: set nano-particles in ultrasonic vibration apart into different solution of nanoparticle in accordance with different concentration, mix the solution with the same volume of organic solution whose concentration is 1/12500 (w/v), make it react in ultrasonic vibration at 37° C. for 1 hour, instill the resultant solution into a spin column (Molecular Probes company) with chromatographic gel, centrifuge it under the condition of 4000 rpm/min, remove the liquid from the collecting tube and make it ready for use (when all conditions are optimized, the process of centrifugal separation can be omitted).

Nano-particle-coated derivatives prepared in the implementation example are listed in Table 4.

TABLE 4

| Nano-particle derivative | Nano-particle | Coating material: Functional high polymer | Coating material: Manufacturer |
|---|---|---|---|
| DEAE-dextran-coated nano-particle | Silicon oxide(Ludox AS-40) | DEAE-dextran | Pharmacia Corp. |
| QAE-cellulose-coated nano-particle | Silicon oxidenano-particle (STN-3) | QAE-cellulose | Chengdu Chenguang Chemical Industry Research Institute |

TABLE 4-continued

| | | Coating material | |
|---|---|---|---|
| Nano-particle derivative | Nano-particle | Functional high polymer | Manufacturer |
| CM-dextran-coated nano-particle | Silicon oxide(Ludox AS-40) | CM-dextran | Pharmacia Corp. |
| Polyvinylpyrrolidone-coated nano-particle | Silicon oxide(Ludox AS-40) | Polyvinyl-pyrrolidone | Tianjin Jinyu Fine Chemical Co., Ltd. |
| Polylysine-coated nano-particle | Silicon oxide nano-particle (STN-3) | Polylysine | Sigma Corp. |
| Amino diazane-polylysine-coated nano-particle | Silicon oxide nano-particle (STN-3) | Amino diazane-polylysine | Chengdu Chempep New Technology Co., Ltd |

Implementation Example 2

The Preparation of Functionalized Nano-particles

The nano-particles used for preparing the functionalized nano-particles in this implementation example include those selected from Table 1 and nano-particle derivatives prepared in Implementation example 1, while the employed functional reagents are selected from the ligands in Table 4.

The preparation of functionalized nano-particles in this implementation example includes the following steps: put nanoparticles or nanoparticle polymers in ultrasonic vibration, prepare them dispersively into nano-particle solution with concentration ranging from 1/6250 to 1/25000 (w/v), mix the solution with ligand solution whose concentration is 1-2 mg/ml (the mixture ratio is 1:1) and make the mixture react for 1 hour at room temperature. If purification is necessary, instill the resultant solution into a spin column (Molecular Probes company) with chromatographic gel, centrifuge it under the condition of 4000 rpm/min, remove it from the collecting tube and make it ready for use. The same method can also be used for preparing functionalized nano-particles that make use of either other nano-particles or functional reagents. The acquired functionalized nano-particles prepared in this example are showed in Table 5.

TABLE 5

| Functionalized nano-particle | Nano-particle | Functional reagent (ligand) |
|---|---|---|
| EBV antigen-STN-3 | Silicon oxide nano-particle (STN-3) | EBV-VCA-P18 antigen |
| HCV Ag-STN-3 | Silicon oxide nano-particle (STN-3) | HCV Ag |
| HIV Ag-STN-3 | Silicon oxide nano-particle (STN-3) | HIV Ag |
| HBs antigen-STN-3 | Silicon oxide nano-particle (STN-3) | HBs antigen |
| EBV antigen-Ludox | Silicon oxide (Ludox As-40) | EBV-VCA-P18 antigen |
| HCV Ag-Ludox | Silicon oxide (Ludox As-40) | HCV Ag |
| HIV Ag-Ludox | Silicon oxide (Ludox As-40) | HIV Ag |
| HBs antigen-Ludox | Silicon oxide (Ludox As-40) | HBs antigen |
| HBs antibody-Ludox | Silicon oxide (Ludox As-40) | HBs antibody |
| HCV Ag-titanium dioxide | Titanium dioxide nano-particle | HCV Ag |
| HIV Ag-titanium dioxide | Titanium dioxide nano-particle | HIV Ag |
| HCV Ag-CDS7 | Hydrophobic silicon nano-particle (CDS7) | HCV Ag |
| HIV Ag-CDS7 | Hydrophobic silicon nano-particle (CDS7) | HIV Ag |
| EBV antigen-colloidal gold | Colloidal gold | EBV VCA-P18 antigen |
| EBV antigen-amino-colloidal gold | Amino-colloidal gold | EBV VCA-P18 antigen |
| HCV Ag-DEAE particle | DEAE-dextran-coated nano-particle | HCV Ag |
| HIV Ag-DEAE particle | DEAE-dextran-coated nano-particle | HIV Ag |
| HCV Ag-QAE particle | QAE-dextran-coated nano-particle | HCV Ag |
| HIV Ag-QAE particle | QAE-dextran-coated nano-particle | HIV Ag |
| HCV Ag-polyvinylpyrrolidone particle | Polyvinylpyrrolidone-coated nano-particle | HCV Ag |
| HIV Ag-polyvinylpyrrolidone particle | Polyvinylpyrrolidone-coated nano-particle | HIV Ag |
| HCV Ag-polylysine particle | Polylysine-coated nano-particle | HCV Ag |
| HIV Ag-polylysine particle | Polylysine-coated nano-particle | HIV Ag |
| HCV Ag-amino diazane lysine particle | Amino-diazane polylysine-coated nano-particle | HCV Ag |

TABLE 5-continued

| Functionalized nano-particle | Nano-particle | Functional reagent (ligand) |
|---|---|---|
| HIV Ag amino diazane lysine particle | Amino-diazane polylysine-coated nano-particle | HIV Ag |

Implementation Example 3

Preparation of Nano-structured Support

The nano-structured support prepared in this example includes the complex of nano-particle/substrate and the complex of nano-particle/micrometer particle. In accordance with the preparation method known publically, nano-particle/micrometer particle/substrate complex can also be prepared. The nano-structured support prepared in this example can be used as analysis-chip substrate, ELISA plates substrate, planar chromatography reagent strips substrate, and chromatography gel respectively.

The solid phase supports used in this example are conventional solid phase supports, including glass slide, 96-well polystyrene plate and nitrocellulose membrane strip in Table 1. The preparation in this implementation is also fit for preparing the conventional solid phase support made of following materials or the derivatives thereof: silica, silica gel, ceramics, metallic oxide, metal, polymer material as well as their complexes. The nano-particles used in this example include inorganic nano-particles (e.g. Silicon oxide nano-particle (STN-3), Silicon oxide (LUDOX AS-40, colloidal silica), Titanium dioxide nano-particle and colloidal gold in Table 1) and their derivatives (e.g. the substance prepared in this implementation example). The said method is also applicable in preparation of organic nano-particles and other inorganic nano-particles, such as: inorganic non-magnetic oxide nano-particles including the particles of alumina oxide, the non-magnetic metal nano-particles including the particles of vanadium, and lead, organic nano-particles including the particles of plastic, polysaccharide, emulsion and resin. The nano-particle derivatives used in this example include the derivatives bound with surface group or/and coating organic compound. And the surface groups include amino-group. The coating organic compound include polyvinylpyrrolidone and dextran derivative.

The surface group of glass slide functional reagent used in the example includes: amino, aldehyde, epoxy and amino diazane. Coating organic compound used in this example includes: polyvinylpyrrolidone and dextran derivatives. The preparation method in this example is also applicable to other derivatives of nano-particle or/and solid phase support, e.g. those with the following surface groups or/and the derivatives of coating organic compounds. The surface group includes one or more types of the following: diethylaminoethyl, diethyl- (2-hydroxypropyl) aminoethyl, carboxymethyl, sulfopropyl, mercaptoethylpyridine, siloxanyl, thioalcohol and alkyl group. The coating organic compound includes one or more types of organisms below: surfactants including the types of TWEEN (polyoxyethylene nonionic detergent), polyelectrolyte including polyamino acid, oleophilic organisms including polysiloxane, ion exchange polymers including dextran derivative, agarose derivative, cellulose derivative, polyacrylamide, and affinity materials including heparin natrium, antigen and antibody.

1) The Preparation of Nano-particle/Substrate Complex (1) The Chip Substrate Preparation by Fixation of Nano-particle Suspension (a) Direct Fixation The slide and other chip substrate in Table 1 are contacted with the suspension of different concentration of nano-particle, selected from Table 3 or 4, for over 2 hours, and then rinse and dry them. Numerous nano-structured chip substrates can be acquired via this method.

(b) Fixation After Activation

Activate nano-particle or/and substrate firstly and then fix the nano-particle on the substrate. For example, nano-particle will undergo activation firstly, which will help it to bind up with functional reagent or/and solid phase support. Then its suspension will be put into contact with the solid phase support so as to have fixation of the activated nano-particle on the substrate; or the solid phase support will undergo activation firstly, which will help it to bind up with the nano-particle or/and the functional reagent. Then the solid phase support will be put into contact with the nano-particle suspension so as to have the nano-particle fixation on the activated substrate.

For example, the glass slide or other chip substrate in Table 1 is contacted with the suspensions of different concentration of nano-particle derivative, prepared in example 1 (Table 4), for over 2 hours, and then rinsed and dried. In another case, the glass slides in Table 1 are treated with 10% concentration of NaOH and HNO3, and then cleaned and dried as activated glass slides, which are then soaked in the nano-particle suspensions of different concentration selected from Table 3 or 4 for over 2 hours, then cleaned and dried. Numerous nano-structured chip substrates can be acquired via this method.

(c) Fixation Before Activation

Put the nano-particle suspension into contact with the solid phase support and obtain fixation reaction first, and then proceed with activation process, which helps immobilize the functional reagent. For example, the glass slides in Table 3 are soaked in the nano-particle suspensions of different concentration selected from Table 3 or 4 for over 2 hours, cleaned and dried afterward and then activated with the method of slide activation. Numerous nano-structured chip substrates can be acquired with this method.

(2) Nano-structured Chip-substrate Preparation by Chemical Cross-linking

The stability of nano-particle fixed on the solid phase support can be increased through chemical cross-linking method, wherein said nano-particle is high-polymer-coated nano-particle. For example, coat the glass slide in Table 3 with DEAE-dextran, then soak them in CM-dextran-coated-silicon oxide nano-particle suspension of different concentration, prepared in example 1, for over 2 hours, have them rinsed and dried and finally cross-link them with dextran by cross-linker epoxy chloropropane. Numerous nano-structured chip substrates of high stability can be acquired via this method.

(3) Nano-structured Chip-substrate Preparation by Heat Treatment

The stability of nano-particle fixed on the solid phase support can also be increased by heat treatment. For example, heat the chip substrate prepared by the fixation of nano-particle suspension in a temperature range between 30° C. and the sintering point of the solid phase support and then cool it down, which can increase its stability of fixation. In comparison with the chip substrate prepared by fixation of nano-particle suspension only, the chip substrate prepared by using heat treatment (e.g. 37° C. over 15 hours, 60° C. over 10 hours, or 150° C. over 1 hours) presents higher fixation intensity in Rhodamine-labeled secondary antibody after both being rinsed supersonically for 1 hour. Numerous nano-structured chip substrates of high stability can be acquired through this method.

(4) The Preparation of Chip Substrate with Nano-structured Channel

The nano-structured region in this invented nano-structured support can be used as transporting channel for fluid. The preparation of chip substrate with nano-structured channel in the implementation example is similar to that of chip substrate mentioned above, except that the chip substrate of this preparation (4) will not be soaked in the nano-particle suspension. Instead, according to the size and position of the channel on the substrate, the nano-particle suspension of different concentration is painted, in optimal quantity and in determined place (e.g. to demarcate the substrate surface with lines whose width is 0.3-1.0 mm, and length 3 mm), onto the substrate surface for reaction for more than half an hour. After that, it is rinsed and dried. The nano-structured region, which is formed on the glass slide substrate by fixing the hydrophilic nano-particle (e.g. LUDOX AS-40, colloidal silica in Table 1, DEAE-dextran-coated nano-particles, QAE-cellulose-coated nano-particles and polyvinylpyrrolidone-coated nano-particles in Table 4), presents a surface-water contact angle, as measurement proves, smaller than that of glass slide substrate, so that it presents a water-drainage function. Though with no intention getting into any theoretical discussion, we would like to say that the invented micro-channel owing to the nano-particle effect thereon (e.g. even larger surface area, more tiny concave objects) is the cause or partially the cause of this kind of "capillary action". Although the micro-channel is simple in this example, the professional of this field can easily prepare variety of micro-channel chips with the micro-channel of this invention, by using other known techniques in micro-channel chip preparation.

(5) The Preparation of Nano-particle Coated Microwell Plate

The substrate used here is a 96-well polystyrene plate for ELISA (Shenzhen Jincanhua Industrial Co., Ltd). The nano-particle used here is colloidal gold, silicon oxide nano-particles (STN-3) and silicon oxide (LUDOX AS-40, colloidal silica) (See Table 1) respectively. The said nano-particle coated microwell plate is prepared as follows: make nano-particle suspension of different concentration contact with the bottom plane of microwell of the polystyrene plate, proceed with the reaction at room temperature for 15 hours, and then rinse the plate repeatedly with distilled water.

The above-mentioned chemical cross-linking method and heat treatment method can also be used for preparing the nano-particle coated microwell plate. Some nano-particle-coated microwell plates prepared in the implementation example are listed in Table 10.

(6) The Preparation of Nano-particle-Coated Planar Chromatography Strips

The key points of this preparation are the same as the preparation of the said nano-particle-coated microwell plates. Some nano-particle-coated planar chromatography strips prepared in the implementation example are listed in Table 11.

2) The Preparation of Nano-particle/Micrometer Particle Complex

The nano-particle/micrometer particle complex prepared in this example is used for preparing analysis-chip, ELISA plate, planar chromatography strip and chromatography gel.

The micrometer particles used here are those listed in Table 3, including conventional chromatography gel such as silica gel (particle size 40-60 μm produced by the Chemical Institute, Chinese Academy of Sciences) and SEPHADEX (macroscopic beads synthetically derived from polysaccharide, dextran) (Pharmacia Corp.). The preparing method here is also applicable to micrometer particles made of the following materials or the derivatives thereof: ceramics, metallic oxides, metals, other polymer materials and their complex, and micrometer particles with nano-particles distributed on the surface.

The nano-particles used here include inorganic nano-particles [e.g. Silicon oxide nano-particles (STN-3), Silicon oxide (LUDOX AS-40, colloidal silica), Titanium dioxide nano-particles and Colloidal gold] and their derivatives (e.g. the prepared chemicals in the implementation example 1). The preparation method here is also applicable to organic nano-particles and other inorganic nano-particles, such as: inorganic non-magnetic oxide nano-particles including the particles of alumina oxide, the non-magnetic metal nano-particles including the particles of vanadium and lead, the organic nano-particles including particles of plastic, polysaccharide, emulsion and resin.

The nano-particle derivatives used in this example include those bound with surface groups or/and coated with organic compounds; the surface groups include amino-groups; the coating organic compounds include polyvinylpyrrolidone and dextran derivatives. In the derivatives of glass slides used in this example, the surface groups include groups of amino, aldehyde, epoxy and amino diazane; coating organic compounds include polyvinylpyrrolidone and dextran derivatives. The method in this example is also applicable to other derivatives of nano-particles or/and solid phase supports, e.g. the derivatives of the following surface groups or/and coating organic compounds: a) The surface groups include one or more of the following chemicals: diethylaminoethyl, diethyl-(2-hydroxypropyl) aminoethyl, carboxymethyl, sulfopropyl, mercaptoethylpyridine, siloxanyl, thioalcohol and alkyl group; b) The coating organic compounds include one or more of the following organisms: surfactants like Tween types, polyelectrolyte like polyamino acid, oleophilic organisms like polysiloxane, ion exchange polymers like dextran derivative, as well as agarose derivatives, cellulose derivatives, polyacrylamides, and affinity materials like heparin natrium, antigens and antibodies.

The key points in preparing the nano-particle/micrometer particle complex are almost the same as those in the preparation of nano-particle/substrate complex mentioned above. The only difference is that micrometer particles are used here to replace the substrates.

3) Evaluation of Nano-structured Supports

In this implementation example, the nano-structure unit and their distribution of the nano-structured unit are characterized by the probe-scanning microscope (SPA-300HV, DFM) and electronic scanning microscope (See Picture 1). In the nano-structured supports prepared in this example, all of the nano-structure units are non-aligned (See Picture 1).

In this implementation example, the height, the minimum size of the cross-section at its half-height, and distribution density of said nano-convex are respectively measured by the probe-scanning microscope (SPA-300HV, DFM) and its analytical software (See Picture 1). In the nano-structured support prepared in this example, when the concentration (w/v) of nano-particle suspension used for coating the solid phase support is 1/250 or 1/175000, the distribution density of said nano-convex, which present the nano-convex height over 3 nm and the cross-section at its half-height being of at least one dimension as 1-500 nm, is less than 10/μm$^2$, even less than 5 nano-convex/μm$^2$. However, when the concentration (w/v) of nano-particle suspension ranges from 1/25000 to 1/50000, the distribution density of said nano-convex, which present the nano-convex height over 3 nm and the cross-section at its half-height being of at least one dimension as 1-500 nm, is more than 10 nano-convex/μm$^2$, even more than 20 nano-convex/μm$^2$.

In this implementation example, the nano-structure covering rate in the nano-structured region is measured by the probe-scanning microscope (SPA-300HV, DFM) and its analytical software (See Picture 1) (the nano-structure covering rate=the surface area of conventional solid phase support coated by nano-stucture/the total surface area of conventional solid phase support). In the nano-structured support prepared in this example, when the concentration (w/v) of nano-particle suspension used for coating support is 1/250 or 1/175000, the nano-structure covering rate in the nano-structured region is less than 30%, even less than 20%. However, when the concentration (w/v) of nano-particle suspension used for coating support ranges from 1/25000 to 1/50000, the nano-structure covering rate is more than 30%, even more than 40%.

In this implementation example, the surface-increasing rate in the nano-structured region is obtained by measuring the specific surface areas of the solid phase support and nano-structured support respectively, and then calculating the ratio between the two (the surface-increasing rate=(the specific surface area of nano-structured support/the specific surface area of the conventional solid phase support therein)×100%, wherein the nano-structured support is prepared by using the said nano particle to coat the whole solid phase support via the said method. In the said nano-structured support prepared in the example, when the concentration (w/v) of nano-particle suspension used for coating support is 1/250 or 1/175000, the surface area increasing rates are less than 300%, even less than 200%. However, when the concentration (w/v) of nano-particle suspension ranges from 1/25000 and 1/50000, the surface area increasing rates are all more than 200%, even more than 300%, and for some individual cases the rate is more than 500%.

In this implementation example, the adsorption-increasing rate of the nano-structured region is obtained through testing the adsorption capacities of the corresponding conventional solid phase support and the nano-structured support respectively (the adsorption-increasing rate=(the adsorption capacity of nano-structured region/the adsorption capacity of the corresponding conventional solid phase support)×100%), wherein the nano-structured support is prepared by using the said nano particle to coat the whole solid phase support via the said method. The test is executed according to the known method, and the static adsorption lasts for 30 minutes at the room temperature. In evaluation of chip substrates, measure their adsorbability for Rhodamine-labeled anti-antibody (IgG labeled by F-6163, Molecular Probes Company). In evaluation of microwell plates for ELISA, measure their adsorbability for enzyme-labeled anti-antibody (by Tiantan Biological Products Co., Ltd.) in the microwelles. In evaluation of nano-particle/micrometer particle complex, measure their adsorbability for albumine (Tiantan Biological Products Co., Ltd.), under the condition that the complex is used as the functional matrix in column chromatography. In the said nano-structured support prepared in the exmaple, when the concentration (w/v) of nano-particle suspension used for coating solid phase support is 1/250 or 1/175000, the adsorption-increasing rate is less than 130%, even less than 115%. However, when the concentration (w/v) of nano-particle suspension ranges from 1/25000 and 1/50000, the adsorption-increasing rate is all more than 115%, even more than 130%, and for some individual cases the rate is more than 180%.

In this implementation example, the adsorption-attenuating rate is obtained through measuring respectively the adsorption decrease in the corresponding solid phase support and the nano-structured support along with the decrease in adsorbates concentration (decrease of each time is measured as 10 time dilution). (The adsorption-attenuating rate=(the adsorption-attenuating velocity of the nano-structured support that decreases with the decreasing lower limit of target concentration/the adsorption-attenuating velocity of the conventional solid phase support that decreases with the decreasing lower limit of target concentration)×100%). Here, the nano-structured support is obtained by using the said nano-particle to coat the whole solid phase support via the said method. The adsorption-attenuating velocity of the decreasing lower limit of target concentration=(adsorption 2−adsorption 1)/(target concentration 2−target concentration 1).

The adsorption is measured in the same way as in the adsorbability measurement mentioned above. In the nano-structured supports prepared in this example, the adsorption-attenuating rate is more than 90%, even near 100%, when the supports are coated with nano-particle suspension whose concentration (w/v) is 1/250 or 1/175000. However, when the supports are coated with nano-particle suspensions whose concentration (w/v) ranges from 1/25000 to 1/50000, the adsorption-attenuating rate is less than 90%, even less than 80%, and for some individual cases the rate is less than 65%.

In this implementation example: the probe-scanning microscope(DFM) analysis is conducted at Analysis & Test Center of Chengdu Electronic Technology University; the electronic scanning microscope analysis is conducted at Analysis & Test Center of Sichuan University; the detection of specific surface area is executed in Analytical laboratory, Organic Chemistry Institute of China Academy of Sciences; the adsorption of chip substrate is tested by the known chip assay methods (Refer to the following implementation examples for details) through the establishment of the standard curve; the adsorption of the microwell plate for ELISA is tested by the known ELISA assay methods (Refer to the following implementation examples for details) through the establishment of the standard curve; the adsorption of nano-particle/micrometer particles is tested by the known chromatography analysis methods (Refer to the following implementation examples for details) through the establishment of the standard curve. Though different measuring instruments and calculation methods may bring about differences in data, still if some values are obviously bigger than others, a comparative study on them might be of significance in principle.

Implementation Example 4

The Preparation of Functionalized Nano-structured Support (1)

The functionalized nano-structured support prepared in this implementation example is the one used for polypeptide analysis, the nano-structured chip in particular. In the invention, the term "nano-structured chip" contains at least a functionalized nano-structured region described in the invention (e.g. a spot in probe micro-array). A chip can possess more than one reactor and a reactor can possess more than one fonctional-reagent-containing spot (probe spot). So long as one spot is of the functionalized nano-structured region of the invention, the chip is considered the invented functionalized nano-structured support or nano-structured chip. The nano-structured chips in this example include complex of functionalized nano-particle/substrate and complex of functionalized nano-particle/micrometer particle/substrates. The nano-structured chips in this example can be applied to other targets, such as drug that can interact with polypeptide (polypeptide-related-drug).

The functional reagents used in this example include polypeptide (e.g. synthetic peptide EBV VCA-P18), antigen (e.g. HCV, HIV and Syphilis antigen), and antibody (e.g. HBs antibody). The method in this example is also applicable to other functional reagents, such as drugs, polysaccharides, vitamins, antibiotics, functional organisms, single-strand or multi-strand DNA, RNA, viruses, cells and their combinations.

The solid phase supports used in this example include conventional solid phase supports and nano-structured supports. The conventional solid phase supports used in this example include the chip substrates in Table 3 (glass slides and the derivatives of glass slides). The preparing method in this example is also applicable to chip substrates made of the following materials or derivatives: silica, silica gel, ceramics, metallic oxide, metal, polymer material as well as their complexes. The nano-structured support in this example is the one containing no functional reagents mentioned-above, and includes the nano-structured chip substrate prepared in Implementation Example 3.

The nano-particles used in this example are the same as those used in Implementation Example 3 (nano-particles in Table 1 and nano-particle derivatives prepared in Implementation Example 1). The method in this example is also applicable to other nano-particles. The functionalized nano-particles used in this example are those prepared in Implementation Example 2. The method in this example is also applicable to other functionalized nano-particles. The micrometer particles used in this example are the same as those in Implementation Example 3 (micrometer particles in Table 3).

The chip prepared in this example is the one with multiple reaction wells, and its preparing method is as follows: paint the place for the partition structure on the chip with high-hydrophobic organic silica coating material (by Chengdu Chenguang Chemical Industry Design Institute), and then dry it to form a painting film with thickness of less than 0.05 mm, so as to form the partition structure of reaction-well(Refer to Chinese Patent Application: Number CN03117397.7). There are 8 reaction-wells on one chip. The size of each is 4.5 mm×4.5 mm, and the width of partition structure between two reaction-wells is 4.5 mm. The method in this example can also be applicable to the chip with single reaction-well.

1) The Preparation of Complex of Functionalized Nano-particle and Substrate (1)

The functionalized nano-particle/substrate complex prepared in this example is the nano-structured support of mono-functional reagent, in which an functionalized nano-structured region contains only one type of functional reagent. The complex includes: substrate coated with ligand-nano-particle, ligand-nano-structure-ligand substrate, and substrate coated with ligand-nano-structure-ligand-nano-particle. The ligand mentioned in this example is used not only as functional reagent but also as linking agent for linking the nano-structure and the substrate, or/and the nano-structures.

(1) Basic Methods (a) Immobilization of the Functional Reagent on the Nano-structured Support Spot the said functional reagent by the arrayer (DY-2003 biology-chip microarrayer) in the pattern of microarray onto the functional reagent-free nano-structured support and obtain the functionalized nano-particle/substrate complex. The spotting method and condition used in this example are the same as the known methods, and numerous nano-structured chips (ligand-nano-particle-coated substrate) can be obtained by this way.

(b) Fixation of the Functionalized Nano-particle on the Conventional or Nano-structured Substrate Make suspension of affinity nano-particle (prepared in Implementation Example 2,See Table 5) with different concentrations, spot them, by employing the arrayer (DY-2003 analysis-chip arrayer), in the pattern of microarray onto the conventional solid phase support (the ligand-nano-particle-ligand-substrate), or onto the nano-structured support (the substrate coated with ligand-nano-particle-ligand-nano-particle), and functionalized nano-particle/substrate complex can be obtained. In the implementation example, the reagent, such as the coupling functional reagent used to fix the functionalized nano-particle, is sometimes fixed onto the substrate. The spotting method and condition used in this example are the same as the known methods, and numerous nano-structured chips can be acquired by this method.

(2) Nano-structured Chip Preparation by Heat Treatment

The stability of the nano-particle fixed on the solid phase support can be increased by heat treatment. For example, the stability of at least part of the chip prepared above can be increased by the heat treatment after the block treatment of the prepared chip with bovine serum albumin: dry it without washing away the protein, and then heat it at 50° C. for 10 hours, and then cool it down. Many known protective agents besides albumin can be used in the heat treatment for functional reagents, such as the sugars (dextran, maltose etc.). The heating conditions should contribute to enhancing not only the stability of nano-structure, but also that of the functional reagent with the protective agent. The enhanced stability of nano-structure is evidenced by some chips (e.g. chip 219 and 220 in Table 7) that undergo heat treatment (e.g. at 37° C. for over 15 hours, at 60° C. over 10 hours, or at 150° C. over 1 hours) in comparison with the corresponding chips without heat treatment. After being rinsed supersonically for 2 hours, the former has a higher stability than the latter. Numerous nano-structured chips with high stability can be acquired by this way.

(3) The Preparation of Chip or Chip Substrate with Functionalized Nano-structured Channel The functionalized nano-structured region in the invented functionalized nano-structured support can be used as fluid-transport channel or/and sample-separation channel. The method of preparing functionalized nano-structured channel in this example is the same as that used in Implementation Example 3. The only difference is that functionalized nano-particle (e.g. the functionalized nano-particles prepared in Implementation Example 2) is used here to replace nano-particles. Although the functionalized channel in this example is simple, the professional can produce various types of chip with functionalized channel of this invention, through combining this example with other known technique.

2) The Preparation of Functionalized Nano-particle/Substrate Complex (2)

The functionalized nano-particle/substrate complex prepared in this example is a nano-structured support with multi-functional reagents, i.e., an functionalized nano-structured support containing two or more types of functional reagents in an functionalized nano-structured region. The nano-structured support with multi-functional reagents includes: ligand②-nano-particle-ligand②-ligand①-nano-particle-ligand①-substrate and ligand②-nano-particle-ligand②-ligand①-substrate, wherein the ligand① can have the coupling reaction with ligand② and therefore bind more easily with substrates than ligand②. One type of ligand in this example (ligand②, e.g. HBsAb) is used not only as functional reagent, but also as linking agent; however, the other (ligand①, e.g. HBsAg) is only used as linking agent.

In this implementation example, the preparation method of ligand②-nano-particle-ligand②-ligand①-nano-particle-ligand①-substrate is as follows: mix the suspension of ligand②-nano-particle-ligand② with that of ligand①-nano-particle-ligand① at the ratio of 1:1 (whose nano-particle concentration are 1/25000 (w/v)), spot the mixture onto the substrate via the routine method to form 3×2 arrays (3 types of functionalized nano-particles, 2 spots for each type), and then make the block treatement with bovine serum albumin solution. The acquired chip is marked as No.223 and the concentration of HBsAb is 3 mg/ml while spotting.

In this implementation example, the preparation method of ligand②-nano-particle-ligand②-ligand①-substrate complex is as follows: mix the suspension of ligand②-nano-particle-ligand② (the nano-particle concentration 1/25000 (w/v)0 with the ligand① at the ratio of 1:1, spot the mixture onto the substrate via the routine method to form 3×2 arrays (3 types of functionalized nano-particles, 2 spots for each type), and then make the block treatement with bovine serum albumin solution. The acquired chip is marked as No.224 and the concentration of HBsAb is 3 mg/ml while spotting.

3) The Evaluation of Functionalized Nano-structured Support

The evaluation methods used in the implementation example are the same as those used in Implementation Example 3, which includes that of: the nano-structure units and their distribution, the nano-convex and its height, the least size of the cross-section at its half-height of nano-convex, the distribution density, by using the probe-scanning microscope (DFM) and the electronic scanning microscope(See picture 2).

In the functionalized nano-structured supports prepared in this example, all of the nano-structure units are non-aligned (See Picture 2). when the suspension concentration (w/v) of fuctionalized nano-particle, used to be spoted on the solid phase support, is 1/250 or 1/175000, the distribution density of said nano-convex, which present the nano-convex height over 3 nm and the cross-section at its half-height being of at least one dimension as 1-500 nm, is less than 10 μm$^2$, even less than 5 nano-convex/μm$^2$, And the nano-structure covering rate of the functionalized region is all less than 30%. However, when the concentration (w/v) ranges from 1/25000 to 1/50000, the distribution density of said nano-convex is more than 10 nano-convex/μm$^2$, even more than 20 nano-convex/μm$^2$. And in this last case, the nano-structure covering rate of the functionalized nano-structured region (spots) of the functionalized nano-structured supports is more than 30%, even more than 40%. Wherein the nano-structure covering rate=the surface area of conventional solid phase support coated by nano-stucture/the total surface area of conventional solid phase support).

In this example, the surface increasing rate of the functionalized nano-structured region is measured in the same way of example 3. The surface increasing rate=(ratio surface area of the functionalized nano-structured region/ratio surface area of the corresponding region on the corresponding conventional solid phase support)×100%. With fewer spots on the chip, the surface area of the functionalized nano-structured region is measured by using a model obtained by coating the whole substrate (e.g. epoxy-group slides in Table 3) with functionalized nano-particles (e.g. (HCV Ag)- Ludox in Table 5), so the corresponding region on the conventional support refers to the whole substrate (e.g. epoxy-group slides). In the said functionalized nano-structured support prepared in the example, when the suspension concentration (w/v) of functionalized nano-particle used for coating substrate is 1/250 or 1/175000, the surface area increasing rates are less than 300%, even less than 200%. However, when the concentration (w/v) ranges from 1/25000 and 1/50000, the surface area increasing rates are all more than 200%, even more than 400%, and for some individual cases the rate is more than 650%.

In this example, the adsorption increasing rate of the functionalized nano-structured region is measured in the same way of example 3. The adsorption-increasing rate=(the adsorption capacity of functionalized nano-structured region / the adsorption capacity of the non-functionalized nano-structured support)×100%). The functionalized nano-structured region is prepared by using a model obtained by coating the whole solid phase support with functionalized nano-particles, which is same as that way mentioned above. In the said functionalized nano-structured support prepared in the example, when the suspension concentration (w/v) (e.g. HCV-Ag) LUDOX (colloidal silica) in Table 5) of functionalized nano-particle used for coating substrate(e.g. epoxy-group slides in Table 3) is 1/250 or 1/175000, the adsorption-increasing rate are less than 130%, even less than 115%. However, when the concentration (w/v) ranges from 1/25000 and 1/50000, the adsorption-increasing rates are all more than 115%, even more than 130%, and for some individual cases the rate is more than 180%.

In the implementation example, the sensibility-increasing rate is measured by comparing the ratio of analytical sensitivities between the functionalized nano-structured region and the non-functionalized nano-structured support that contains the same conventional solid phase support and functional reagent: the sensibility-increasing rate=(sensitivity of the functionalized nano-structured region/sensitivity of the non-functionalized nano-structured support)×100%.

In the implementation example, the model of nano-structured chips refers to those prepared by spotting the suspension of functionalized nano-particle whose concentration ranges from 1/25000 to 1/50000 (w/v) onto the substrate (e.g. epoxy-group glass slide in Table 3), while possessing the features of the functionalized nano-structured region mentioned-above. The model chip of non-functionalized nano-structured support refers to those prepared by loading the same functional reagent onto the same substrate under the same condition. In preparing the nano-structured chip in the example, when the suspensions of functionalized nano-particle whose concentration (w/v) is 1/250 or 1/175000 are used to coat the substrate, the sensitivity-increasing rate is below 150%, even below 120%. However, when the suspensions of same functionalized nano-particle whose concentration (w/v) ranges from 1/25000 to 1/50000 are used to coat same substrate, the sensitivity-increasing rate is over 120%, even over 150%, and in some individual cases, it could be over 600%.

In the implementation example, the signal-attenuated rate is measured by respectively testing the signal-attenuated rate of nano-structured chip and non-nano-structured chip containing the same substrate and functional reagent, as the lower limit of target concentration decreases. Signal-attenuated rate=(attenuation velocity of identifiable signal of the functionalized nano-structured region that moves along with the decreasing lower limit of target concentration/the attenuation velocity of identifiable signal of the non-functionalized nano-structured support that moves along with the decreasing lower limit of target concentration)×100%, wherein the attenuation velocity of identifiable signal that moves with the decreasing lower limit of target concentration=(identifiable signal②-identifiable signal ①/(target concentration②- target concentration ①). The identifiable signals (e.g. the reading on the confocal fluorescein scanner of the fluorescein-labeled targets captured by functionalized nano-structure) can be measured by the known chip measuring method. In preparing the nano-structured chip in the example, when the nano-particle suspensions whose concentration (w/v) is 1/250 or 1/175000 are used to coat the substrate, the signal-attenuated rate is more than 70%, even more than 90%. However, when the suspensions of functionalized nano-particles whose concentration (w/v) ranges from 1/25000 to 1/50000 are used to coat the same substrate, the signal-attenuated rate is less than 90%, even less than 70%, and in some individual cases, it could be ess than 50%.

In the implementation example, the adsorption-attenuated rate=(adsorption attenuation velocity of the functionalized nano-structured region that moves with the decreasing lower limit of target concentration/adsorption attenuation velocity of the non-functionalized nano-structured support that moves with the decreasing lower limit of target concentration) X 100%). It is measured in the same way as in implementation example 3, that is, taking the whole solid phase support coated with functionalized nano-particles by the said method as the functionalized nano-structured region.

In preparing the functionalized nano-structured support in this example, when the nano-particle suspensions ((HCV Ag)- LUDOX (colloidal silica) in Table 5) whose concentration (w/v) is 1/250 or 1/175000 are used to coat substrates (e.g. epoxy slides in Table 3), the adsorption-attenuated rate is more than 80%, and even more than 90%. However, when the suspensions of same nano-particle whose concentration (w/v) ranges from 1/25000 to 1/50000 are used to coat the same substrates, the adsorption-attenuated rate is less than 90%, even less than 80%, and in some individual cases, it could be less than 70%.

Though different measuring instruments and calculation methods may bring about differences in data, still if some values are obviously bigger than others, a comparative study on them might be of significance in principle.

Implementation Example 5

Preparation of Functionalized Nano-structured Support (2)

The functionalized nano-structured support prepared in the implementation example is that used for nucleic acid analyses, and the nano-structured chip in particular is designed for such a purpose. It can also be applicable to other targets, such as nucleic-acid-interactive drugs.

The functional reagents used in the implemntation example include single-strand or multi-strand DNA, RNA, and viruses. The solid phase support and nano-particle used here are the same as those in Implementation Example 4. The preparing method in the example is the same as in that in Implementation Example 4.

The evaluation method in this example is the same as that in Implementation Example 4. The functionalized nano-support prepared in the example produces the same result as the functionalized nano-support prepared with the same method in Implementation Example 4. When the substrate is coated with suspensions of functionalized nano-particle whose concentration (w/v) ranges from 1/25000 to 1/50000, the obtained results are as follows: in appearance, the nano-structure units are all non-aligned; the distribution density of the nano-convex is more than 18 nano-convex/$\mu m^2$, which the nano-convex presents a height over 3 nm and the cross-section at its half-height presents at least one dimension as 1-500 nm; In features, the covering rate of nano-structure is more than 70%; the surface-increasing rate is more than 450%; the adsorbability-increasing rate is more than 160%; the adsorption-attenuated rate is less than 70%.

Implementation Example 6

Preparation of Functionalized Nano-structured Support (3)

The functionalized nano-structured support prepared in the implementation example is the compelx of functionalized nano-particles/micrometer particles, which can be used for preparing analysis-chips or chromatography gel.

The functional reagents used in the example include polypeptides (e.g. synthetic peptide EBV VCA-P18), antigens (e.g. HCV, HIV and Syphilis antigen), and antibodies (e.g. HBs antibody). The method in the example is also applicable to other functional reagents, such as drugs, polysaccharides, vitamins, antibiotics, functional organisms, single-strand or multi-strand DNA, RNA, viruses, cells and their combinations.

The micrometer particles used in the example are those listed in Table 3, including conventional chromatography gel: silica gel (particle size 40-60 μm, by Chemical Institute, Chinese Academy of Sciences), and SEPHADEX (macroscopic beads synthetically derived from polysaccharide, dextran) (by Pharmacia Corp.). The preparing method in the example is also applicable to micrometer particles made of the following materials or their derivatives: ceramics, metallic oxide, metals, other polymer materials and their complexes, as well as micrometer particle coated with nano-particles.

The nano-particles used in the example are the same as those used in Implementation Example 3 (nano-particles listed in Table 1 and nano-particle derivatives prepared in Implementation Example 1). The method in the example is also applicable to other nano-particles. The functionalized nano-particle used in the example is the one prepared in Implementation Example 2. The method in the example is also applicable to other functionalized nano-particles. The micrometer particle used in the example is the same as that used in Implementation Example 3 (micrometer particles listed in Table 3).

1) Preparing Method

Three methods in the example are adopted to prepare the functionalized nano-particle/micrometer particle complex: a) coat functional reagents onto the nano-particle/micrometer particle complex prepared in Implementation Example 3; b) prepare the complex of functionalized nano-particles/micrometer particles by mixing the functionalized nano-particles prepared in Implementation Example 2 with other particles according to the method specified in Implementation Example 3 for preparing nano-particle/micrometer particle complex; c) coat the functionalized nano-particles prepared in Implementation Example 2 onto the complex of the nano-particles/micrometer particles in Implementation Example 3 according to the method specified in Implementation Example 3 for preparing nano-particle/micrometer particle complex. In the implementation example, functional reagent is coated onto the nano-particle/micrometer particle complex in accordance with the known methods, e.g. the method of coating functional reagent onto micrometer particles in the preparation of affinity chromatography gel.

2) Evaluation Method

The evaluation method in this implementation example is the same as that of Implementation Example 4. The functionalized nano-particle support prepared in the example produces a result similar to that of functionalized nano-particle support prepared with same method in Implementation Example 4. For example, in this implementation, complexes of HCV Ag) LUDOX (colloidal silica)/silica gel and (HCV Ag) LUDOX (colloidal silica)/SEPHADEX (macroscopic beads synthetically derived from polysaccharide, dextran) are obtained by coating silica gel and SEPHADEX A50 (macroscopic beads synthetically derived from polysaccharide, dextran) with HCV Ag) LUDOX (colloidal silica) respectively. When suspensions of the same functionalized nano-particles whose concentration ranges (w/v) from 1/25000 to 1/50000 are employed in the preparation, the following results are obtained: in part appearance, the nano-structure units are all non-aligned; the distribution density of the nano-convex is more than 15 nano-convexes/$\mu m^2$, which the nano-convex presents a height over 3 nm and the cross-section at the nano-convex half-height presents at least one dimension as 1-500 nm; in features, the covering rate of nano-structure is more than 50%; the surface increasing rate is more than 350%; the adsorbability-increasing rate is more than 130%; the adsorption-attenuated rate is less than 80%.

Implementation Example 7

Preparation of Nano-particle Marker

The complex of marking functionalized reagent, nano-particles, and molecular labeling material prepared in this implementation example is used as the nano-particle marker for the chip application.

The labeling active reagent used in the example include polypeptides, such as HCV antigens and goat-anti-human secondary antibody (by Beijing Tiantan Biological products Co., Ltd.). The method in the example is also applicable to other labeling active reagent, e.g. drugs, polysaccharides, vitamins, antibiotics, functional organisms, single-strand or multi-strand DNA, RNA, viruses, cells and their combinations.

Not a labeling enhancer itself, the nano-particle used in the example is the non-magnetic inorganic non-metal particle with a particle diameter 1-100 nm, including inorganic non-metal nano-particles in Table 1 and the derivatives of these inorganic non-metal nano-particles prepared in Implementation Example 1. The method in the example is also applicable to other non-magnetic inorganic non-metal nano-particles. The functionalized nano-particles used in the example are those based on non-magnetic inorganic non-metal nano-particles prepared in Implementation Example 2. The micrometer particles used in the example are the same as those in Implementation Example 3 (the micrometer particles listed in Table 3). The molecular labeling material in the example is Rhodamine (by Molecular Probes Company.). The method in the example is also applicable to other labeling materials, e.g. fluorescent material, chemiluminescent material, chemiluminescent catalyst, colored metal salt, dye and pigment.

The marker of contrastin the implementation example is a routin marker not treated with nano-particle liquid (Rhodamine-labeled goat anti-human secondary antibody, by Jackson ImmunoResearch Laboratories, USA)

1) Arrangement

The preparing method of the complex of ligand-molecule labeling material in the implementation example is the known method of preparing the Rhodamine-labeling anti-antibody.

The preparing method of functionalized nano-particles in this implementation example is as follows: set nano-particles in ultrasonic vibration, made them dispersively into nano-particle suspensions whose concentration ranges from 1/50 (1/125) to 1/10000 (1/25000) (w/v), mix the solutions with marking functionalized reagent solution whose concentration is 2 mg/ml at 1:1 ratio respectively, and proceed with the reaction at room temperature away from light for 2 hours. The method of purifying the mixture is: instill the mixed resultant into a spin column (Molecular Probes company) filled with gel, centrifuge it under the condition of 4000 rpm and remove the liquid from the collecting tube for use.

The method of preparing the complex of nano-particle-molecular labeling material in this implementation example is as follows: set nano-particles in ultrasonic vibration, made them dispersively into nano-particle suspensions whose concentration is 1/1000 (1/125) (w/v), mix the solutions with molecular labeling material solution whose concentration is 2 mg/ml at 1:1 ratio respectively, and proceed with the reaction at room temperature for 1 hour. If necessary, the method of purifying the mixture is: instill the mixed resultant into a spin column (Molecular Probes company) filled with gel, centrifuge it under the condition of 4000 rpm and remove the liquid from the collecting tube for use.

2) Preparation of the Complex of Ligand/Nano-particle/Molecule Labeling Material In the preparation method of this Implementation Example, the combination of the said ligand, molecular labeling material and nano-particles includes one or more of the following ways: a) combine the functionalized nano-particles with molecular labeling material; b) combine the said nano-particle-molecular labeling material with ligand; c) combine molecular labeling material and ligand prepared by the known method with nano-particles; d) combine ligand, molecular labeling material and nano-particle simultaneously, wherein the resultant can be either mixture or purified substance. Table 6 contains part of the complex of ligand/nano-particle/molecular labeling material prepared in the example.

3) Comparison

The chips employed in this implementation example are prepared by the known chip preparating method (substrates are epoxy glass slids, and ligands are hepatitis C virus antigens (HCV Ag) and human immunodeficiency virus antigens (HIV Ag) respectively.)

The comparative method used here is the same as that of chip application in Implementation Example 10. Table 6 contains the comparative results among part of the markers prepared in the implementation example, which indicates that the sensitivity of markers of this example is obviously improved in comparison with the marker of contrast at least.

method of the implementation example is also applicable to other catalysts, e.g. enzyme catalyst. The colorants used in the example include silver compound ($AgNO_3$) and crystal violet. The said method is also applicable to other metal compounds and dyes.

The preparing methods of the complex of labeling active reagent/nano-structure/calalyst, the complex of labeling active reagent/nano-structure/calalyst and colorant, and the complex of labeling active reagent/nano-structure/colorant are the same as those in Implementation Example 7.

For the details of the preparation of labeling active reagent/colorant complex in the implementation example, refer to the relevant documents (<<A quantitative or qualitative test method for target in the sample and their testing device>> Chinese patent application number: CN03117645.3).

TABLE 6

| | | | Test result | | | |
|---|---|---|---|---|---|---|
| Marker | Nano-particle | Preparing method | Dilution multiple | Sample 1 | Sample 2 | Sample 3 |
| Marker of the contrast | No | | 200 | + | + | – |
| Marker of the contrast | No | | 400 | – | – | – |
| Marker 1 | Silicon oxide nano-particle (STN-3) | (A) | 400 | + | + | – |
| Marker 2 | Silicon oxide nano-particle (STN-3) | (B) | 400 | + | + | – |
| Marker 3 | Silicon oxide nano-particle (STN-3) | (C) | 400 | + | + | – |
| Marker 4 | Silicon oxide nano-particle (STN-3) | (D) | 400 | + | + | – |
| Marker 5 | Polyvinylpyrrolidone-coated nano-particle | (C) | 400 | + | + | – |
| Marker 6 | Amino diazane-polylysine-coated nano-particle | (C) | 400 | + | + | – |

Implementation Example 8

Preparation and Application of Chip Marking System (1)

The chip marking system prepared in the implementation example comprises marker, colorant, and optionally, color-contrastling agent and color stabilizer.

1) Preparation

The chip markers prepared in the implementation example are the following respectively:

① the complex of mark functionalized reagent/nano-structure/calalyst;

② the complex of labeling active reagent/nano-structure/calalyst and colorant;

③ the mixtures of ① and the complex of labeling active reagent/nano-structure/colorant or the complext of labeling active reagent/colorant.

The labeling active reagent, nano-particle and functionalized nano-particle used in the implementation example are the same as those in Implementation Example 7. The catalyst used in the example is the amino-group colloidal gold particle (2020) (Nanoprobes Corp.), whose diameter is 1.4 nm. The Mixtures of the said complexes need certain volume ratios to produce.

2) Application

HIV/HCV antigen chip is made by spotting HIV antigen and HCV antigen on an epoxy-group glass slide by the known method. The positive serum of the contrast (the mixture of HIV antibody-positive serum and HCV antibody-positive serum) and negative serum of the contrast (the mixture of HIV antibody-negative serum and HCV antibody-negative serum) of different concentration (PBS buffer solution is diluent) are added respectively. After one-hour reaction at room temperature, the reactors are washed, and added respectively with the various said markers (e.g. amino-group colloidal gold/silicon oxide nano-particle/anti-human secondary antibody complex, amino-group colloidal gold/silicon oxide nano-particle/crystal violet/anti-human secondary antibody complex) and markers of the contrast (colloidal gold-labeled goat anti-human secondary antibody). After 10-minute reaction, the reactors are again washed and added with Glutaric dialdehyde whose concentration is 2.5%. Then according to the instruction manual about silver enhancer (by Sigma), the mixture of solution A and solution B is added and the reaction is triggered. Then sodium thiosulfate is used to halt the reaction.

Then the chip is washed and observed by naked eyes with the following results: with all the markers, the positive contrast serum which is diluted 5000 times presents positive result (black spots); with the invented marker, the negative contrast serum which is diluted 10 times presents negative result (without black spots); while with marker of the contrast, under the same condition, positive result (black spots) can be observed. The results suggest that the method by using the invented marker possesses a higher specificity.

Implementation Example 9

Preparation of Chip Marking System (2)

The chip marking system prepared in the implementation example comprises marker, colorant, and optionally, color-contrastling agent and color stabilizer.

1) Preparation

The chip markers prepared in the implementation example respectively are: ① the mixture of functional reagent/catalyst complex and functional reagent/colorant, ② the mixture of functional reagent/catalyst complex and functional reagent/nano-structure/colorant, and ③ the mixture of labeling active reagent/nano-structure/catalyst complex and labeling active reagent/nano-structure/colorant complex.

The labeling active reagent, nano-particle, functionalized nano-particle, catalyst and colorant used in this implementation example are the same as those in Implementation Example 8.

The preparing methods of ① labeling active reagent/nano-structure/calalyst complex, ② labeling active reagent/nano-structure/catalyst and colorant complex, ③ labeling active reagent/nano-structure/colorant complex in this implementation example are the same as those in Implementation Example 7.

For the details of the preparation of labeling active reagent/colorant complex in the implementation example, refer to the relevant documents (dye marker patent application <<A quantitative or qualitative test method for target in the sample and their testing device>> Chinese patent application number: 03117645.3).

The labeling active reagent/colorant complex in this implementation example is the goat anti-human anti-antibody labeled by nanometer gold of a size of 1.4 nm (by Nanoprobes Corp.).

Mixtures of the said complexes need certain volume ratios to produce.

2) Application

HIV/HCV antigen chip is made by spotting HIV antigen and HCV antigen onto an epoxy-group glass slide by the known method. The positive contrast serum (the mixture of HIV antibody-positive serum and HCV antibody-positive serum) and negative contrast serum (the mixture of HIV antibody-negative serum and HCV antibody-negative serum) of different concentration (PBS buffer solution is diluent) are added respectively. After one-hour reaction at room temperature, reactors are washed, and added respectively with the various said markers (e.g. amino-group colloidal gold/silicon oxide nano-particle/crystal violet/anti-human secondary antibody complex, the mixture of Amino colloidal gold/anti-human secondary antibody complex and crystal violet/anti-human secondary antibody complex) and markers of the contrast (colloidal gold-labeled goat anti-human secondary antibody). After 10-minute reaction, the reactors are again washed and added with Glutaric dialdehyde whose concentration is 2.5%. Then according to the instruction manual about silver enhancer (by Sigma), the mixture of solution A and solution B is added and the reaction is triggered. Then sodium thiosulfate is used to halt the reaction. Then the chip is washed and observed by naked eyes with the following results: with all the markers, the positive contrast serum which is diluted 5000 times presents positive result (black spots); with the invented marker, the negative contrast serum which is diluted 15 times presents negative result (without black spots); while with marker of the contrast, under the same condition, positive result (black spots) can be observed. The results suggest that the method by using this invented marker possesses a higher specificity.

Implementation Example 10

Preparation and Application of Chip Kit (1)

1) Preparation of Chip Kit

The kit in this implementation example comprises the invented nano-structured chip prepared in Implementation Example 4.

2) Application of Chip Kit

In this implementation example, Sample 1 is HCV antibody-positive serum, Sample 2 is $HCV_{1+2}$ antibody-positive human serum, and Sample 3 is negative contrast (negative contrast serum of HCV antibody and $HCV_{1+2}$ antibody). All samples are analyzed previously with the classical ELISA method when the serum is 20-time-diluted. The marker in this implementation example is Rhodamine-labeled goat anti-human secondary antibody (by Jackson ImmunoResearch Laboratories, Inc. USA).

In experiment, the mentioned above 3 types of samples are added respectively into the reaction-wells of the chip listed in Table 7. Wherein the contrast chip is prepared by immobilizing the same ligand via the routine spotting method onto an epoxy group glass slide listed in Table 3. The adding amount is 15 μl and the reaction time is 30 minutes. Then wash it for 5 times with 25 μl of washing solution added each time. Then 15 μl of marker is added. After the reaction, the cell (well) is washed for 5 times, with 25 μl of washing solution added each time. Then it is dried and scanned with the laser power/gain set at 35/50. The scanner used herein is a laser confocal scanner (a GMS 418 microarray scanner by Afymetrix corp.), with 532 nm exciting-light wavelength and 570 nm emitting-light wavelengths. The read signals are processed with software (JAGUAR II) and negative (−) or positive (+) results can be decided by compararing the average value of the results with the Cut-off value (See Table 7). The test results indicate that the nano-structured chip of the invention presents a higher sensitivity.

TABLE 7

| Chip No. | Ligand/nano-particle/substrate complex: Substrate | ligand or functionalized nano-particle | Test result: Sample 1 | Sample 2 | Sample 3 | Sample dilution |
|---|---|---|---|---|---|---|
| Contrast | Aldehyde group glass slide | ligand | + | + | − | 100-times |
| Contrast | Aldehyde group glass slide | ligand | − | − | − | 500-times |
| ligand-nano-particle-ligand-substrate complex | | | | | | |
| 201 | Aldehyde group glass slide | Ligand colloidal gold | + | + | − | 500-times |
| 202 | Aldehyde group glass slide | (Ligand-amino)-colloidal gold (2020) | + | + | − | 500-times |
| 203 | Aldehyde group glass slide | DEAE-dextran coated nano-particle with ligand | + | + | − | 500-times |
| 204 | Aldehyde group glass slide | Polyvinyl pyrrolidone-coated nano-particle with ligand | + | + | − | 500-times |
| 205 | Aldehyde group glass slide | amino diazane-polylysine coated nano-particle with ligand | + | + | − | 500-times |
| 206 | Aldehyde group glass slide | Ligand hydrophobic silicon oxide nano-particle (CDS7) | + | + | − | 500-times |
| 207 | Epoxy group glass slide | Ligand silicon oxide nano-particle (STN-3) | + | + | − | 500-times |
| 208 | Epoxy group glass slide | Ligand silicon oxide (LUDOX AS-40 colloidal silica) | + | + | − | 500-times |
| 209 | Epoxy group glass slide | Ligand porous silicon oxide (AEROSIL 200) | + | + | − | 500-times |
| 210 | Epoxy group glass slide | Ligand titanium oxide nano-particle | + | + | − | 500-times |
| 211 | Epoxy group glass slide | DEAE-dextran coated nano-particle with ligand | + | + | − | 500-times |
| 212 | Epoxy group glass slide | Ligand Polyvinylpyrrolidone-coated nano-particle | + | + | − | 500-times |
| 213 | Epoxy group glass slide | amino diazane-polylysine coated nano-particle with ligand | + | + | − | 500-times |
| 214 | Epoxy group glass slide | Ligand hydrophobic silicon oxide nano-particle (CDS7) | + | + | − | 500-times |
| 215 | Amino diazane glass slide | Ligand hydrophobic silicon oxide nano-particle (CDS7) | + | + | − | 500-times |

TABLE 7-continued

| | Ligand/nano-particle/substrate complex | | Test result | | | |
|---|---|---|---|---|---|---|
| Chip No. | Substrate | ligand or functionalized nano-particle | Sample 1 | Sample 2 | Sample 3 | Sample dilution |
| 216 | Amino diazane glass slide | Ligand silicon oxide nano-particle (STN-3) | + | + | − | 500-times |
| 217 | Amino diazane glass slide | Ligand silicon oxide (LUDOX AS-40, colloidal silica) | + | + | − | 500 times |
| 218 | Amino diazane glass slide | amino diazane-polylysine coated nano-particle with ligand | + | + | − | 500 times |
| 219 | PVP-coated glass slide | Ligand hydrophobic silicon oxide nano-particle (CDS7) | + | + | − | 500 times |
| 220 | PVP-coated glass slide | Ligand silicon oxide nano-particle (STN-3) | + | + | − | 500 times |
| 221 | PVP-coated glass slide | Ligand silicon oxied (LUDOX AS-40, colloidal silica) | + | + | − | 500 times |
| 222 | PVP-coated glass slide | amino diazane-polylysine coated nano-particle with ligand | + | + | − | 500 times |
| Ligand-nano-particle-ligand-nano-particle-substrate complex | | | | | | |
| 223 | Substrate 2 | Ligand silicon oxide (LUDOX AS-40, colloidal silica) | + | + | − | 500 times |
| 224 | Substrate 2 | Amino diazane-polylysine coated nano-particle with ligand | + | + | − | 500 times |

In the table, the ligands are HIV antigen and HCV antigen respectively.

Implementation Example 11

Preparation and Application of Chip Kit (2)

1) Preparation of Chip Kit

The chip kit in this implementation example contains complex of ligand/nano-particle/molecular labeling material. It is the same complex prepared in Implementation Example 7. The chip in the kit is the contrast in Implementation Example 10. Thus numerous different kinds of kits can be made in accordance with this implementation example.

2) Application of Chip Kit

In this implementation example, the employed sampling and testing methods are the same as those in Implementation Example 10. With the invented marker, positive results can be observed from the positive serum which is diluted 500 times; whereas with the marker of the contrast, negative result can be observed under the same condition. The results therefore suggest that the method of using this invented marker presents a higher specificity.

Implementation Example 12

Preparation and Application of Chip Kit (3)

1) Preparation of Chip Kit

The kit in this implementation example comprises the invented nano-structured chip mentioned in Implementation Example 4 and the invented marking system containing complex of ligand/nano-particle/molecular labeling material in Implementation Example 7. Thus numerous kits of different kinds can be made in accordance with this implementation example.

In this implementation example, the employed sampling and testing methods are the same as those in Implementation Example 10. The results are showed in Table 8.

TABLE 8

| | The composition of kit | | Sample dilution | Test results | | |
|---|---|---|---|---|---|---|
| Test | Chip | Marker | multiple | Sample 1 | Sample 2 | Sample 3 |
| 1 | Contrast | Marker of the contrast | 200 | + | + | + |
| 2 | Contrast | Marker of the contrast | 500 | − | − | + |
| 3 | Nano-structure chip | Marker of the contrast | 500 | + | + | + |
| 4 | Nano-structure chip | Marker of the contrast | 600 | − | − | + |
| 5 | Contrast | Marker 3 | 400 | + | + | + |
| 6 | Contrast | Marker 3 | 600 | − | − | + |
| 7 | Nano-structure chip | Marker 3 | 600 | + | + | + |

Implementation Example 13

Preparation and Application of Chip Kit (4)

1) Preparation of Chip Kit

The kit in this implementation example comprises magnetic chips. The magnetic nano-particles used in this implementation example are those present in the water-based magnetic solution (NG-21A) in Table 1; the substrate is an epoxy-group glass slide in Table 3; the ligand is the used in Implementation Example 2, namely, hepatitis C virus antigen (HCV Ag) and HIV1+2 antigen.

(1) Preparation of Magnetic Nano-particles Chip

The magnetic nano-particle chip in this implementation example is a ligand/magnetic nano-particle/substrate complex.

The said chip is the one with multiple reactors, wherein the preparation of multi-well-substrate is the same as that in the implementation example 4. The affinity magnetic nano-particle is prepared as the functionalized nano-particle prepared in the implementation example 2.

Spot the prepared affinity magnet nano-particles containing hepatitis C virus antigen (HCV Ag) (1 mg/ml) and HIV1+2 antigen (1 mg/ml) respectively into the wells of the multi-well substrate, form 2×2 arrays with 2 spots on each of the affinity magnet nano-particles, and proceed with the reaction at 37° C. for 1 hour under the effect of the external magnetic field, which help drive affinity magnetic nano-particles toward the substrate and therefore become fixed on it. Once the coating is completed, the chip is blocked with bovine serum albumin solution for use.

The Chip contrast in this implementation example is the one prepared by spotting hepatitis C virus antigen (HCV Ag) (1 mg/ml) and $HIV_{1+2}$ antigen (1 mg/ml) without magnetic nano-particle onto aldehyde group substrate by the known spotting method.

(2) Preparation of Magnetic Nano-particle Markers

The magnetic nano-particle marker in this implementation example is a complex of ligand/magnetic nano-particle/molecular labeling material, in which ligand is goat anti-human secondary antibody (by Jackson ImmunoResearch Laboratories, Inc.).

3) Preparation of Magnetic Chip Kit

The magnetic chip kit in this implementation example can comprise one, two, three or four types of components concluding magnetic particle, which are respectively the said magnetic nano-particle chips, said magnetic nano-particle markers, said affinity magnetic nano-particles (blocked with bovine serum albumin), and magnetic nano-particles (blocked with bovine serum albumin). Different combinations of components can form different kits (See Table 9 for details).

4) Application of Magnetic Chip Kit

The magnetic chip kit in this implementation example is used to test the negativeness or positiveness of $HIV_{1+2}$ antibody and HCV antibody in a sample serum. The serum samples here are the same as those in Implementation Example 2. However, the testing method is different from the known method and the difference lies in: when the kit contains other components of magnetic particles (e.g. magnetic nano-particle) in addition to the magnetic chip, the reaction is performed at the bottom of the chip under the effect of the external magnetic field, especially the stable pulsating magnetic field. With such a external magnetic effect, markers of magnetic nano-particles and the target captured by affinity magnetic nano-particles are apt to move toward the bottom of the reactor. And with the effect of pulsating magnetic field, the magnetic nano-particles added to the sample are apt to join the liquid, thus helping to drive the liquid sample to flow so as to have a better mixture. Since there are a variety of kits, we will only take one kit as an example to explain its application. The application of other kits can be analogized according to this example.

The components of the kit used in this implementation example are as follows: contrast chip, magnetic nano-particles and affinity magnetic nano-particles, wherein the magnetic nano-particles and affinity magnetic nano-particles are respectively mixed with 4 types of serum samples (after the blending, the concentration of the magnetic nano-particles is 1/2000 (W/V) whereas the affinity magnetic nano-particles is 1/4000 (W/V)). In the application prodecure, add 15 ul of serum sample into the chip reaction-well, let it react at 37° C. for 10 minutes with the effect of pulsating magnetic field, then wash it before adding 15 μl of magnetic nano-marker, let it react for 10 minutes at 37° C. with the effect of pulsating magnetic field, wash and dry it, and then proceed with scanning and analysis through the same method described in Implementation Example 10. Results obtained are showed in Table 9.

TABLE 9

| | kit composition | | | | | | Sample dilution | Test result | | |
|---|---|---|---|---|---|---|---|---|---|---|
| Test | I | II | III | IV | V | VI | multiple | Sample 1 | Sample 2 | Sample 3 |
| 1 | ✓ | | | | | ✓ | 100 | + | + | − |
| 2 | ✓ | | | | | ✓ | 400 | − | − | − |
| 3 | | ✓ | | | | ✓ | 400 | + | + | − |
| 4 | | ✓ | | | | | 400 | + | + | − |
| 5 | | ✓ | ✓ | ✓ | | | 400 | + | + | − |
| 6 | | ✓ | ✓ | ✓ | ✓ | | 400 | + | + | − |
| 7 | ✓ | | ✓ | | | | 400 | + | − | − |

TABLE 9-continued

| | kit composition | | | | | | Sample dilution | Test result | | |
|---|---|---|---|---|---|---|---|---|---|---|
| Test | I | II | III | IV | V | VI | multiple | Sample 1 | Sample 2 | Sample 3 |
| 8 | ✓ | | | ✓ | | | 400 | + | + | − |
| 9 | ✓ | | | | ✓ | | 400 | + | + | − |

In the table:
I - chip of contrast,
II - chip with magneticle nano-particle,
III - magnetic nano-particle,
IV - affinity magnetic nano-particle,
V - marker of magnetic nano-particle,
VI - marker of contrast

Implementation Example 14

Preparation and Application of Kit for the Quantitative or/and Qualitative Detection of Polypeptides (1)

1) Preparation of Kit

The kit in this implementation example is ELISA kit with functionalized nano-structured support.

The ligand used here is synthetic peptide, which is EBV-VCA-P18 antigen prepared through the known method as indicated in the following document: Tranchand-Bunel, D., Auriault, C., Diesis, E., Gras-Masse, H. (1998) Detection of human antibodies using "convergent" combinatorial peptide libraries or "mixotopes" designed from a nonvariable antigen: Application to the EBV viral capsid antigen, p18, J. Peptide Res. 52, 1998, 495-508. The nano-structured ELISA plate used in this implementation example is prepared by immobilizing ligand onto the bottom of micropores in the said nano-structured microwell plate.

(1) Functionalized Nano-structured Support Prepared by Coating the Support with Nano-particles Refer to Implementation Example 3 for the preparation and evaluation of nano-structured microwell plates. Coat 0.3 μg/ml concentration synthetic peptide onto the said nano-particle-coated microwell plates (colloidal gold-coated microwell plate, silicon oxide-coated microwell plate and silicon oxide nano-particle-coated microwell plate) and the microwall plate of contrast (96-well polystyrene plate) respectively via the routine method of preparing ELISA plate, coat 8 wells on each of the plates and block them with bovine serum albumin solution for use.

The ELISA plate of contrast in this implementation example is the ELISA plate taking the 96-welled plate as substrate and coated with the EBV-VCA-P18 antigen via the said method.

(2) Functionalized Nano-structured Support Made of Functionalized Nano-particles The methods of preparing functionalized nano-particle containing EBV-VCA-P18 antigen and silicon oxide nano-particle (STN-3) are the same as those in Implementation Example 2.

With the known ELISA plate-coating method, the functionalized nano-particle, whose concentration of EBV VAS-P18 is 0.1 μg/ml, and concentration of nano-particle is 1:25000 (w/v), is coated into 8 microwells of 96-welled microplate in Table 3. After that, the 8 microwells are blocked by bovine serum albumin solution for use.

2) Application

The samples in this implementation example are EBV IgA positive serum and EBV IgA negative serum. All samples have been pre-assayed by the classical ELISA method under reaction condition where serum is diluted 20 times.

In experiment, add the two types of the samples into the said ELISA plate of contrast and 3 nano-structured ELISA plates respectively, 4 reaction-wells for each sample. When loaded, the samples are diluted adequately. Add 100 μl of sample each time and set the reaction temperature at 37° C. Wash them 3 times with 300 μl of washing solution added each time. Add 100 μl marker (the enzyme-labeled goat anti-human IgA by Beijing Tiantan Biological Products Co., Ltd) and let the reaction temperature at 37° C. for 30 minutes. Herein the substrate added will react under the same condition as under the classical ELISA method. Then a colorimetric analysis by the ELISA plate reader (Thermo Labsystems, by Shanghai Lab Analytical Instrument Co., Ltd.) will be conducted to decide whether the average results of 8 wells present negative result (−) or positive result (+) based on the Cut-off value, as showed in Table 10.

TABLE 10

| | ELISA plate | | | |
|---|---|---|---|---|
| | ELISA plate of contrast | ELISA plate 1 | ELISA plate 2 | ELISA plate 3 |
| Substrate | 96-welled microplate | Colloidal gold-coated microplate | Silicon oxide-coated microplate | Silicon oxide nano-particle-coated microplate |
| Coated nano-particle | No | Colloidal gold | Silicon oxide (LUDOX AS-40, colloidal silica) | Silicon oxide nano-particle (STN-3) |
| Test result with 20-times-dilution (reaction time: 30 minutes) | | | | |
| Sample 1 | + | + | + | + |
| Sample 2 | − | − | − | − |
| Test result with 50-times-dilution (reaction time: 30 minutes) | | | | |
| Sample 1 | − | + | − | + |
| Sample 2 | − | − | − | − |

As indicated in Table 10, the nano-structured ELISA plate is more sensitive and quicker than the ELISA plate of contrast.

Implementation Example 15

Preparation and Application of Quantitative or/and Qualitative Detection of Polypeptides (2)

The kit in this implementation example is a rapid test kit containing functionalized nano-structured supports.

1) Preparation of Kit (1) Preparation of the Nano-particle-coated Planar Chromatography Strips The substrates used in this implementation example are nitrocellulose film strips (by Fujiang Quanzhou ChanglLi Biochemical Co., Ltd) and nylon cellulose film strips (by Fujiang Quanzhou Changli Biochemical Co., Ltd). The nano-particles are silicon oxide nano-particles (STN-3) (by Zhejiang Zhoushen Mingri Nanomaterials Co., Ltd.) and silicon oxide (LUDOX AS-40, colloidal silica) (Sigma-Aldrich Corp.).

The preparation of nano-particle-coated planar chromatography strips in this implementation example is as follows: make nano-particle suspension whose concentration ranges from 1/12500 to 1/25000 (w/v) contact with substrates, continue reacting at room temperature for 5 hours and then wash it repeatedly with distilled water.

The Substrate of contrast is nitrocellulose filmstrips and nyloncellulose film strips which are not treated by the nano-particle buffer solution.

(2) Preparation of Rapid Test Strips of Functionalized Nano-structured Supports

The ligand used in this implementation example is hepatitis C virus antigen (HCV Ag) (by Hepatopathy Institute, People's Hospital of Beijing).

In preparation, spot 0.5-mg/ml-concentration Hepatitis C virus antigen (HCV Ag) onto the 4 types of nano-structured planar chromatography strips and 2 types of substrate of contrasts (detection line) respectively, load rabbit anti-goat IgG respectively to form the quality control line via the routine method, block them with bovine serum albumin solution, and then add the sampling region, marking region with colloidal gold-labeled goat anti-human antibody, and water-absorbing region to form an assemblage.

The rapid test strip of contrast is that prepared from the substrate of contrast therein.

2) Application

In this implementation example, Sample 1 and Sample 2 are HCV antibody positive serum and HCV antibody negative serum respectively. All samples have been beforehand checked by the classical ELISA method to assure their positiveness or negativeness.

In experiment, add the two samples into the 6 types of the said rapid test strips respectively (the sample must be diluted adequately and the loading amount is 50 μl), and then add washing solution immediately till the quality control line appears on the test strip. The results are shown in Table 11.

TABLE 11

| | Nano-structured planar chromatography strip | | Test | | |
|---|---|---|---|---|---|
| Rapid test strip | Conventional substrate | Nano-particle coated | Sample 1 | Sample 2 | Test time needed |
| Test strip of contrast | Nitrocellucose film strip | No | + | − | 2 minutes |
| Rapid test strip coated with nano-particle | Nitrocellucose film strip | Silicon oxide (Ludox AS-40) | + | − | 1 minute |
| Rapid test strip coated with nano-particle | Nitrocellucose film strip | Silicon oxide nano-particle (STN-3) | + | − | 1 minute |
| Test strip of contrast | Nyloncellucose film strip | No | + | − | 2 minutes |
| Rapid test strip coated with nano-particle | Nyloncellucose film strip | Silicon oxide (LUDOX AS-40, colloidal silica) | + | − | 1 minute |
| Rapid test strip coated with nano-particle | Nyloncellucose film strip | Silicon oxide nano-particle (STN-3) | + | − | 1 minute |

As indicated by the results in Table 11, the rapid test strip coated with nano-particle takes only half of the time needed by test strip of contrast.

Implementation Example 16

Preparation and Application of Functionalized Nano-Structured Support as Separating Media The separating media prepared in this implementation example is a fixed phase for chromatography.

1) Preparation

The ligand used in this implementation example is DEAE-dextran (by Pharmacia Corp.); the nano-particle used herein is silicon oxide nano-particles (STN-3) listed in Table 1; the support used herein is silica gel particle for chromatography with average diameter 60 μm (by Chemical Institute, Chinese Academy of Sciences).

In preparation, mix DEAE-dextran solution whose concentration is 1/1000000 (w/v) with silicon oxide nano-particle (STN-3) whose concentration is 1/6250 (w/v), stir the solution for 4 hours at room temperature, then add the pre-dried silica gel particles into it, then proceed with the dextran cross-link according to the method published by one of co-inventors of this invention (Refer to the article "Coated silica supports for high-performance affinity chtomatography of proteins", Journal of Chromatography, 476 (1989) 195-203), and obtain the complex of DEAE-dextran/nano-particle/silica gel particle. Actually, due to the introduction of nanometer dextran, a variety of fixed phase for chromatography can be obtained by method of the classical dextran derivation.

There are other preparing methods for DEAE-dextran/silica gel particle complex as contrast, and for details refer to the method by one of the co-inventors of this invention mentioned above.

2) Application of Lagand/Nano-particle/Support Complex as Separating Media

This implementation example has measured the human albumin dynamic adsorptive capacity of the said silica gel particles, DEAE-dextran/silica gel particle complex and DEAE-dextran/nano-particle/silica gel particle complex, the adsorptive capacities are respectively 1.2 mg/ml, 7.8 mg/ml and 13.5 mg/ml, wherein the DEAE-dextran/nano-particle/silica gel particle complex presents the highest dynamic adsorptive capacity.

Implementation Example 17

Detection of HIV Nucleic Acid Analysis-Chip

1. The Preparation of HIV Chip

The chip used in the implementation example is the invented nano-structured chip, wherein the substrate is the epoxy-group glass slide (See Table 3); the functional reagents are the 8 unclassified target genes in HIV virus conservative regions (6 in Region SK, 1 in Region P, 1 in Region C); the functionalized nano-particle is coated silicon oxide with functional reagents (Ludox AS-40). The functionalized nano-particle is prepared in the same way as in Implementation Example 2, while the preparation and evaluation of nano-structured chips are the same as in Implementation Example 4.

2. Arrangement of Sample

Extract DNA via the conventional method from blood sample that has been inactivated by boiling for 10 minutes, heat the extracted DNA up to 98° C., cool it instantly down to 4° C. or below, and then treat it with denaturing buffer solution. Then remove the denaturing buffer solution, add labeling buffer solution, label the treated DNA with Rhodamine, then remove the free Rhodamine when the labeling reaction is completed, by the method of centrifugal chramatography and make it ready for use.

3. Detection

Mix the labeling DNA sample derived from the above-mentioned 2 blood samples with hybrid solution (the adding ratios are respectively 1:9; 1:99; 1:199), load the 6 diluted samples whose concentration are different into 6 chips (4 reaction-wells for each sample), put them into a moist case for reaction (the reaction time is 60 minutes and the temperature is 42° C.), then the chips out and wash them with buffer solution 3 times, then wash again with alcohol and put aside for drying. Scan them with a laser confocal scanner and obtain the final results from the image processing software. Table 12 contains the overall evaluations of 4 reaction-wells in a chip with multiple spots.

TABLE 12

| Test | Chip | Times of Sample dilution | Test result |
|---|---|---|---|
| 1 | Chip of contrast | 10 | + |
| 2 | Chip of contrast | 100 | − |
| 3 | Chip of contrast | 400 | − |
| 4 | Nano-structured chip | 10 | + |
| 5 | Nano-structured chip | 100 | + |
| 6 | Nano-structured chip | 400 | − |

What is claimed is:

1. A nano-structured support for analysis or/and separation, said nano-structured support comprising a nano-structured region,
said nano-structured region comprising a solid phase support and a nano-structure fixed on said solid phase support,
said nano-structure comprising non-aligned nano-structure units,
said nano-structure units including nano-convex portions with a height over 3 nm, which cross-section at its half-height presents at least one dimension as 1-500 nm,
wherein said nano-structured region has:
1) a distribution density of said nano-convex portions of more than 10 convexes/$\mu m^2$;
2) a sensibility-increasing rate of more than 200%; and
3) any one or more of the following characteristics:
   (1) a nano-structure covering rate of more than 30%;
   (2) a surface-increasing rate of more than 400%;
   (3) an adsorption-increasing rate of more than 150%; and
   (4) an adsorption-attenuating rate of less than 80%,
wherein said analysis or/and separation includes polypeptide or/and polypeptide-related-drug analysis or/and separation,
wherein said nano-structure includes:
(1) an inorganic nano-particle at least including:
silica nano-particle or alumina oxide nano-particle; and/or
2) an organic nano-particle; and/or
3) a derivative of the inorganic and/or the organic nano-particle, which includes a derivative of inorganic and/or organic nano-particle which has bound chemical surface group and/or a coated organic compound;
wherein said bound chemical surface group includes one or more of following chemical surface groups selected from the group consisting of amino-, aldehyde-, epoxy-, amino diazane, diethylaminoethyl, diethyl- (2-hydroxyproptyl) aminoethyl, carboxymethyl, sulfopropyl, mercaptoethylpyridine, siloxanyl, thioalcohol- and alkyl-;
wherein said coated organic compound includes one or more of the following substances:
(1) a surfactant including polyvinylpyrrolidone and/or nonionic surfactant;
(2) a polyelectrolyte including polyamino acid;
(3) an oleophilic compound including polysiloxane;
(4) an ion exchange polymer including dextran derivative, agarose derivative, cellulose derivative, and/or polyacrylamide; or
(5) affinity materials including heparin natrium, antigen and/or antibody;
wherein said nano-structure units are in the shape of a tree branch
and wherein said nanostructure support is prepared by the steps comprising
1) contacting a suspension of nano-particles with said support; and
2) fixing said nano-particles on said support, wherein said suspension has a concentration of from 1/20000 to 1/60000 g/ml in nano-particle weight/volume concentration.

2. The nano-structured support of claim 1, including:

1) a nano-particle/substrate complex;

2) a nano-particle/micro-particle complex; or 3) a nano-particle/micro-particle/ substrate complex.

3. The nano-structured support of claim 1, wherein the nano-structured region has an adsorption-increasing rate of more than 150%.

4. The nano-structured support of claim 1, wherein the nano-structured region has an adsorption-attenuating rate of less than 80%.

5. The nano-structured support of claim 1, wherein said suspension has a concentration of from 1/20000 to 1/50000 g/ml in nano-particle weight/volume concentration.

6. A method for preparing said nano-structured support of claim 1, comprising:

1) contacting a suspension of nano-particles and said solid phase support; and 2) fixing said nano-particles on said conventional solid phase support, wherein said suspension has a concentration of from 1/20000 to 1/60000 g/ml in nano-particle weight/volume concentration.

7. The method of claim 6, further comprising a chemical cross-linking treatment after said fixing step.

8. The method of claim 6, further comprising, after said fixing step, a heat treatment comprising heating and sequential cooling, wherein said heating is processed at over 30° C., but at below a sintering point of said solid phase support.

9. A polypeptide-functionalized nano-structured support for analysis or/and separation, said polypeptide-functionalized nano-structured support comprising:

a polypeptide-functionalized nano-structured region, said polypeptide-functionalized nano-structured region being formed from a solid phase support and a polypeptide-functionalized nano-structure fixed on the solid phase support, the binding between said polypeptide-functionalized nano-structure and the solid phase support being established through one or more following ways: covalent bond linking, non-specific physicochemical adsorption, antigen-antibody adsorption, or affinity adsorption, said functionalized nano-structure comprising non-aligned nano-structure units and a functional reagent bound thereon, said functionalized nano-structure unit including nano-convex portions with a height over 3 nm, which cross-section at its half-height presents at least one dimension as 1-500 nm, wherein said functionalized nano-structured region has:

1) a distribution density of said nano-convex portions of more than 10 nano-convexes /$\mu m^2$;

2) a sensibility-increasing rate of more than 200%;

3) any one or more of the following characteristics:

(1) a nano-structure covering rate of more than 30%;

(2) a surface-increasing rate of more than 400%, and/or an adsorption-increasing rate of more than 150%; and (3) a ratio of signal-attenuated rates of less than 70%, and/or a ratio of adsorption-attenuated rates of less than 80%, wherein said analysis or/and separation includes polypeptide or/and polypeptide-related-drug analysis or/and separation; and wherein said nano-structure units are in the shape of a tree branch and wherein said functionalized nanostructure support is prepared by the steps comprising 1) contacting a suspension of functionalized nano-particles with said support; and 2) fixing said functionalized nano-particles onto said support, wherein said suspension has a concentration of from 1/20000 to 1/60000 g/ml in nano-particle weight/volume concentration.

10. The functionalized nano-structured support of claim 9, including a nano-structured analysis-chip.

11. The functionalized nano-structured support of claim 9, including:

1) a nano-structured ELISA plate;

2) a nano-structured planar-chromatography reagent strip; or 3) a functionalized nano-structured matrix for separation, including functionalized nano-structured chromatography gel.

12. The functionalized nano-structured support of claim 9, wherein said functionalized nano-structured support is a complex of functionalized nano-particles and the support, wherein said nano-particles have a diameter of 1-100 nm, said nano-particles have one or more of the functional reagents and/or a linking agent immobilized thereon, and said solid phase support is a nano-structured support or a non-nano-structured support.

13. The functionalized nano-structured support of claim 12, wherein said nano-particles include:

1) inorganic nano-particles including at least one selected from the group consisting of magnetic metal nano-particles, non-metal nano-particles, non-magnetic metal nano-particles and non-metal inorganic nano-particles, 2) organic nano-particles, or 3) derivatives of inorganic and/or organic nano-particles which have a chemical group or coating organic compound bound on the nano-particles' surface.

14. The functionalized nano-structured support of claim 13, wherein said non-magnetic inorganic nano-particles include oxide nano-particles selected from the group consisting of silica oxide nano-particles, titanium oxide nano-particles and alumina oxide nano-particles.

15. The functionalized nano-structured support of claim 13, wherein said non-magnetic inorganic nano-particles include non-magnetic non-metal inorganic nano-particles or non-metal inorganic nano-particles formed from silica.

16. The functionalized nano-structured support of claim 13, wherein said chemical group includes one or more of following chemical surface groups selected from the group consisting of amino-, aldehyde-, epoxy-, amino diazane, diethylaminoethyl, diethyl- (2-hydroxypropyl) aminoethyl, carboxymethyl, sulfopropyl, mercaptoethylpyridine, siloxanyl, thioalcohol- and alkyl-; and 2) said organic compound includes one or more of the following substances:

(1) a surfactant including polyvinylpyrrolidone and/or nonionic surfactant;

(2) a polyelectrolyte including polyamino acid;

(3) an oleophilic compound including polysiloxane;

(4) an ion exchange polymer including dextran derivative, agarose derivative, cellulose derivative, and/or polyacrylamide; or (5) affinity materials including heparin natrium, antigen and/or antibody.

17. The functionalized nano-structured support of claim 9, wherein said functional support includes an antibody or an antigen.

18. The functionalized nano-structured support of claim 17, wherein said antibody includes Hepatite B virus surface antibody.

19. The functionalized nano-structured support of claim 17, wherein said antigen includes one or more antigen groups selected from the group consisting of HCV antigen, HIV antigen, HBs antigen and EBV-VCA-P18 antigen.

20. The functionalized nano-structured support of claim 13, including at least one of:

1) a functional reagent/ nano-structured substrate complex; or 2) a functional reagent / nano-structured micro-particle complex.

21. The functionalized nano-structured support of claim 9, including a nano-structured analysis chip.

22. The functionalized nano-structured support of claim 9, including:

1) a nano-structured ELISA plate;

2) a nano-structured planar-chromatography reagent strip; or 3) a functionalized nano-structured matrix for separation, including functionalized nano-structured chromatography gel.

23. The polypeptide-functionalized nano-structured support of claim 12, wherein said diameter of the nano-particle is less than 50 nm.

24. The nano-structured support of claim 9, wherein the nano-structured region has a ratio of signal-attenuated rates of less than 70%.

25. The nano-structured support of claim 9, wherein the nano-structured region has a ratio of adsorption-attenuated rates of less than 80%.

26. The nano-structured support of claim 9, wherein said suspension has a concentration of from 1/20000 to 1/50000 in nano-particle weight/volume concentration.

27. A method of preparing said functionalized nano-structured support of claim 9, comprising:

1) A contacting suspension of functionalized nano-particles and said support; and 2) fixing said functionalized nano-particle on said support, wherein:

said suspension has a concentration of from 1/20000 to 1/60000 g/ml in nano-particle weight/volume concentration;

said contacting refers to point-contact whose contact diameter is less than 0.5 mm, or surface-contact whose contact diameter is more than 0.5 mm.

28. The method of claim 27, comprising also a chemical cross-linking after said fixing.

29. The method of claim 27, comprising also, after said fixing step, a heat treatment comprising heating and sequential cooling, wherein said heating is processed at over 30° C., but at below a sintering point of the said support.

* * * * *